(12) United States Patent
Xia

(10) Patent No.: US 11,998,714 B2
(45) Date of Patent: Jun. 4, 2024

(54) TATTOO NEEDLE AND TATTOO DEVICE

(71) Applicant: Tingting Xia, Jiangsu (CN)

(72) Inventor: Tingting Xia, Jiangsu (CN)

(*) Notice: Subject to any disclaimer, the term of this patent is extended or adjusted under 35 U.S.C. 154(b) by 0 days.

(21) Appl. No.: 18/243,097

(22) Filed: Sep. 6, 2023

(65) Prior Publication Data

US 2023/0414915 A1    Dec. 28, 2023

Related U.S. Application Data

(63) Continuation of application No. PCT/CN2022/071557, filed on Jan. 12, 2022.

(30) Foreign Application Priority Data

Apr. 14, 2021   (CN) .......................... 202110402475.3

(51) Int. Cl.
*A61M 37/00*   (2006.01)
(52) U.S. Cl.
CPC .............................. *A61M 37/0084* (2013.01)
(58) Field of Classification Search
CPC .......... A61M 37/0076; A61M 37/0086; A61M 2202/0007; A61M 2205/106; A61M 2205/8281; A61M 2210/04; A61M 5/46
See application file for complete search history.

(56) References Cited

U.S. PATENT DOCUMENTS

| | | | | |
|---|---|---|---|---|
| 4,798,582 A | * | 1/1989 | Sarath ................... | B43K 1/003 |
| | | | | 604/47 |
| 7,695,486 B2 | * | 4/2010 | Dixon ............... | A61M 37/0076 |
| | | | | 606/186 |
| 2017/0266045 A1 | * | 9/2017 | Kangastupa ............ | A61M 5/46 |
| 2019/0217072 A1 | * | 7/2019 | Xiao ................. | A61M 37/0084 |

FOREIGN PATENT DOCUMENTS

| | | |
|---|---|---|
| CN | 108042905 A | 5/2018 |
| CN | 207520450 U | 6/2018 |
| CN | 209286492 U | 8/2019 |
| CN | 213131574 U | 5/2021 |

OTHER PUBLICATIONS

International Search Report of PCT Patent Application No. PCT/CN2022/071557 dated Apr. 7, 2022.

* cited by examiner

*Primary Examiner* — Robert A Lynch

(57) ABSTRACT

A tattoo needle includes: a needle piercing portion. The needle piercing portion includes at least one piercing projection, wherein each of the at least one piercing projection comprises at least one substrate and a plurality of needle teeth. The number of the at least one substrate is one, the plurality of needle teeth is arranged on a side surface of the one substrate, the plurality of needle teeth are arranged in a row on the substrate, a central axis of each of the plurality of needle teeth is perpendicular to the side surface of the one substrate; and the one substrate is configured to limit a piercing depth that the plurality of needle teeth pierces into a skin.

19 Claims, 30 Drawing Sheets

TATTOO NEEDLE AND TATTOO DEVICE

CROSS REFERENCE TO RELATED APPLICATIONS

The present application is a continuation of PCT patent application No. PCT/CN2022/071557, filed on Jan. 12, 2022, which claims the benefit of Chinese Patent Application No. 202110402475.3 filed on Apr. 14, 2021. All the above are hereby incorporated by reference in their entirety.

TECHNICAL FIELD

The present disclosure relates to the field of tattoo tools, and in particular to a tattoo needle and a tattoo device.

BACKGROUND

Tattoo is a make-up method that breaks and colours the skin. Colour pigments are introduced into the skin and reaches a certain depth in the skin to be retained for months to years. In the art, semi-permanent tattoos are the major demand. The semi-permanent tattoo refers to the colour pigments being retained at a shallower layer of the skin, i.e., at a layer between the epidermis and the dermis or at a layer of the dermis near the epidermis. The semi-permanent tattoo may be metabolized naturally within 1-2 years.

Currently, in order to obtain a colour block, a colour strip or a colour dot, a tattooist may generally use a device having multiple needles in a row to achieve the above tattoo pattern. However, for the device in the art having multiple needles in a row, vibration may occur between adjacent needle filaments, resulting in the colour pigments being splashed around, affecting the tattoo operation. Further, for the device in the art, the needles may pierce into the skin excessively deeply, the colour pigments may spread to a region out of a target region of the skin, resulting in the colour pigments turning blue and being retained in the skin for several years, i.e., resulting in the "colour fading" effect. When the needles pierce into the skin excessively deeply, for the device in the art having multiple needles in a row, needle tips may be bent easily, and skin damage may be caused, the skin may be coloured slowly, the operation to colour the skin may be prolonged, the skin may have a long repairing period, a rate of skin infection may be improved, and colour retention may be reduced.

Furthermore, the device in the art having multiple needles in a row, when being used, may be held by the tattoo by hand, the device pierces into the skin based on naked eye and experience of the tattooist. Therefore, a piercing depth of the device cannot be controlled scientifically, tattoo accidents may be caused easily.

Further, the device in the art having multiple needles in a row may not be destroyed easily after usage. While the device is being detached and discarded, the device may hurt other people, causing contact contamination. Even the device may be reused, generating a risk of blood disease transmission.

Therefore, it is urgent to provide a new technical solution to solve the above technical problems.

SUMMARY OF THE DISCLOSURE

In order to solve the problems in the art, the present disclosure provides a tattoo needle and a tattoo device, the technical solutions are as follows.

A tattoo needle includes: a needle piercing portion. The needle piercing portion includes at least one piercing projection, wherein each of the at least one piercing projection includes at least one substrate and a plurality of needle teeth. The plurality of needle teeth is arranged on a side surface of the one substrate, the plurality of needle teeth is arranged in a row on the substrate, a central axis of each of the plurality of needle teeth is perpendicular to the side surface of the one substrate; and the one substrate is configured to limit a piercing depth when the plurality of needle teeth pierces into a skin.

A tattoo needle includes a liquid guiding member and a needle piercing portion arranged at an end of the liquid guiding member. The liquid guiding member includes a liquid guiding post, the liquid guiding post includes a capillary liquid storage unit to store liquid, the liquid guiding post is configured to guide liquid flow to the needle piercing portion. When the needle piercing portion pierces into a surface of a skin, the liquid is being capable of being introduced into the surface of the skin.

A tattoo device includes the above-mentioned tattoo needle and an external drive member. The external drive member is configured to drive the liquid guiding member of the introduction needle to move.

The present disclosure further provides a tattoo device including the above-described introduction needle.

BRIEF DESCRIPTION OF THE DRAWINGS

In order to more clearly illustrate the technical solutions in the embodiments of the present disclosure or in the art, the accompanying drawings for the description of the embodiments or the art will be briefly introduced below. Obviously, the accompanying drawings in the following description are only some of the embodiments of the present disclosure. Any ordinary skilled person in the art may obtain other drawings based on the accompanying drawings without creative work.

Figure 1:
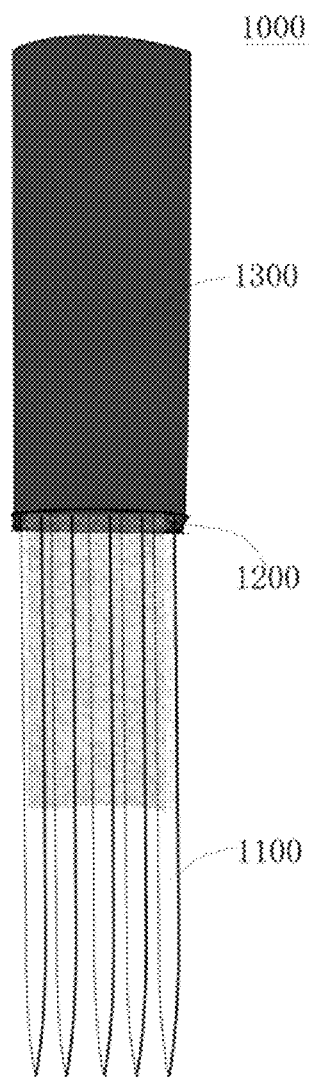
FIG. 1 is a schematic view of a device, in the art, having multiple needles arranged in a row.

Reference numerals are as follows: 100—Introduction needle;
- 110—liquid guiding member; 111—liquid guiding post; 1111—first end face; 1112—second end face; 112—connecting rod; 113—flat-end needle filament; 114—small post; 115—channel;
- 120—capillary liquid storage unit;
- 130—liquid storage structure; 131—fiber filament; 140—needle piercing portion; 141—piercing projection; 1411—substrate; 1412—needle tooth;
- 150—case; 151—fastening end; 152—intermediate connecting tube; 153—needle outlet end; 1531—needle outlet port;
- 160—limiting structure; 161—limiting hole; 162—limiting tube; 163—limiting plate; 164—bracket;
- 170—elastic member;

DETAILED DESCRIPTION

The technical solutions of the embodiments of the present disclosure will be described clearly and completely in the following by referring to the accompanying drawings. Obviously, the described embodiments show only a part of but not all of the embodiments of the present disclosure. All other embodiments obtained, based on the embodiments of the present disclosure, by any ordinary skilled person in the art without making creative work shall fall within the scope of the present disclosure.

In the description of the present disclosure, it is to be understood that any orientation or positional relationship indicated by the terms "top", "bottom", "top", "bottom", "inside", "outside", and so on, is an orientation or a positional relationship as shown in the accompanying drawings. The terms are used only to facilitate and simplify the description of the present disclosure, but do not indicate or imply that the device or element referred to must have a particular orientation or must be constructed and operated in a particular orientation. Therefore, the terms cannot be interpreted as limiting the present disclosure. In the present disclosure, the term "a plurality of" means two or more, unless otherwise expressly and specifically limited.

In the present disclosure, unless otherwise expressly provided and limited, the terms "mounted", "connected", "coupled", "fixed", and so on, shall be understood in a broad sense. For example, connection may be fixed connection, detachable connection, or two elements being configured as a one-piece structure; or may be mechanical connection or electrical connection; or may be direct connection, indirect connection through an intermediate medium, or two elements being internally connected or being interactive with each other. Any ordinary skilled person in the art shall understand specific meanings of the above terms in the present disclosure in a case-by-case manner.

The present disclosure will be illustrated in the following by referring to the drawings and the embodiments.

In order to colour the skin by block, by strip and by dot, the tattoo device in the art mainly takes a single row of metal needle filaments having sharpened tips as operating ends. Further, the single row of needle filaments is welded to a needle handle and are fixed to the tattoo rod through a fixed end of the needle handle. In this way, a device having a row of needles is formed. Usually, the device having a row of needles is used perform following three types of colouring methods. For a method 1, the device streaks a line to colour the skin. That is, the single row of needle filaments forms a longitudinal column, the row of needle filaments breaks the skin successively and repeatedly streak the broken skin, such that a coloured strip is obtained. For a method 2, the device sweeps the skin to colour the skin. That is, the single row of needle filaments are arranged into a horizontal column and move at the same time side-by-side. The single row of needle filaments repeatedly sweep the broken skin, such that a coloured block is obtained. For a method 3, the device pricks the skin at a dot to colour the skin. That is, the single row of needle filaments vertically face the skin, front ends of the needle filaments form a straight line parallel to the skin and repeatedly move up and down to pierce the skin, such that a row of coloured dots are obtained.

However, the above device having a row of needles has poor ink absorption and storage capacity. The device cannot be supplied with the ink for a long time. Therefore, a high rate of empty needles may be caused. Further, elastic vibration between adjacent needle filaments may be caused, resulting in colour pigments being sprayed around and a poor colouring effect.

As shown in FIG. 1 to FIG. 6, schematic views of the device having a row of needles in the art being used in various application scenarios are shown. The drawings show a device 1000 having a row of needles, metal needle filaments 1100; a welding zone 1200; a fixed end 1300; and a skin 2000. As shown in FIG. 1, the device 1000 having a row of needles in the art is shown and includes a plurality of metal needle filaments 1100 and the fixed end 1300 fixed to the tattoo rod. Each of the plurality of metal needle filaments 1100 has a sharpened end. The plurality of metal needle filaments 1100 are welded to the welding zone 1200 and are spaced apart from each other equidistantly. For the device 1000 having a row of needles in the art, a length of each needle tip exposed out of the welding zone is generally in a range of 3 mm-30 mm, which is much greater than the thickness of the epidermis of the human face. An average thickness of the epidermis of the human face is in a range of 0.2-1.0 mm.

Figure 2:
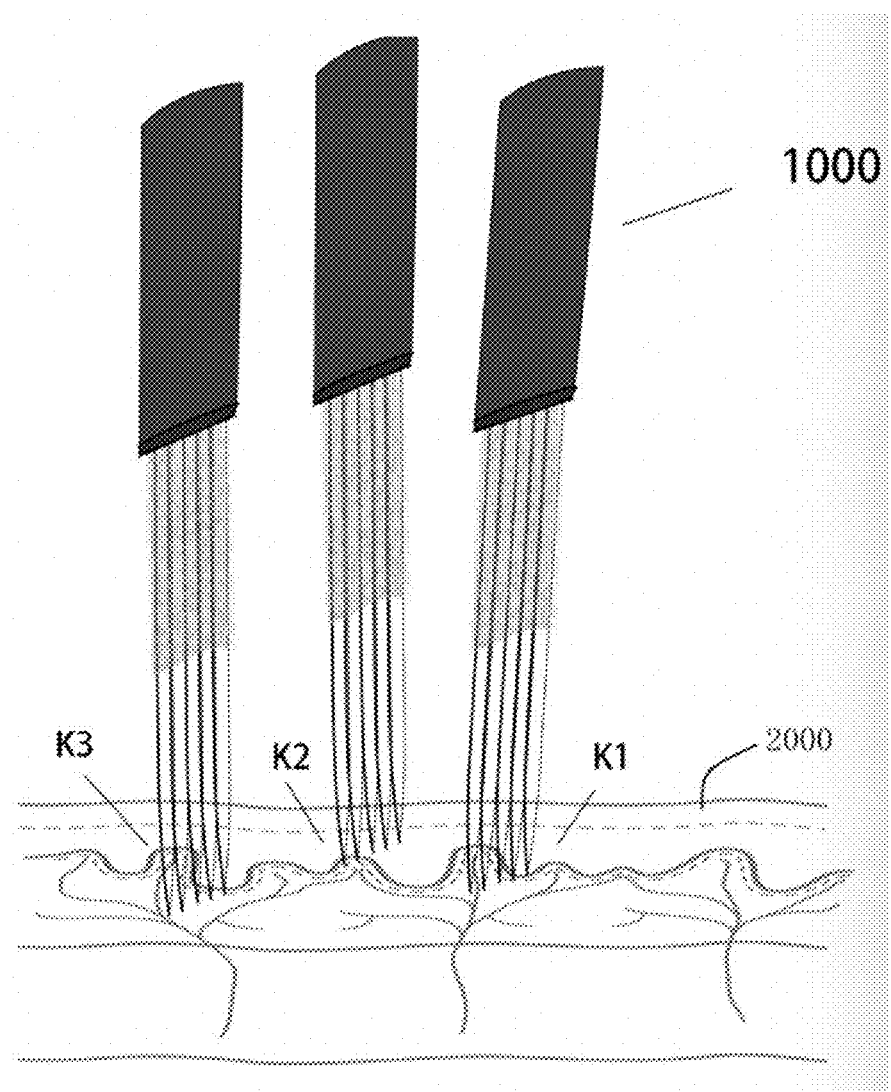
FIG. 2 is a schematic view of an in-use state of the device having multiple needles arranged in a row, as shown in FIG. 1, piercing into the skin.

As shown in FIG. 2, since a piercing depth into the skin is not determined, when the device 1000 having a row of needles is operating to apply colour to the epidermis 2000, the device may pierce to reach depths K1, K2, and K3 under the skin, where the depths K1, K2, and K3 are different from each other. Therefore, the skin may be colour unevenly or darker, or "colour fading" may be caused.

Figure 3:
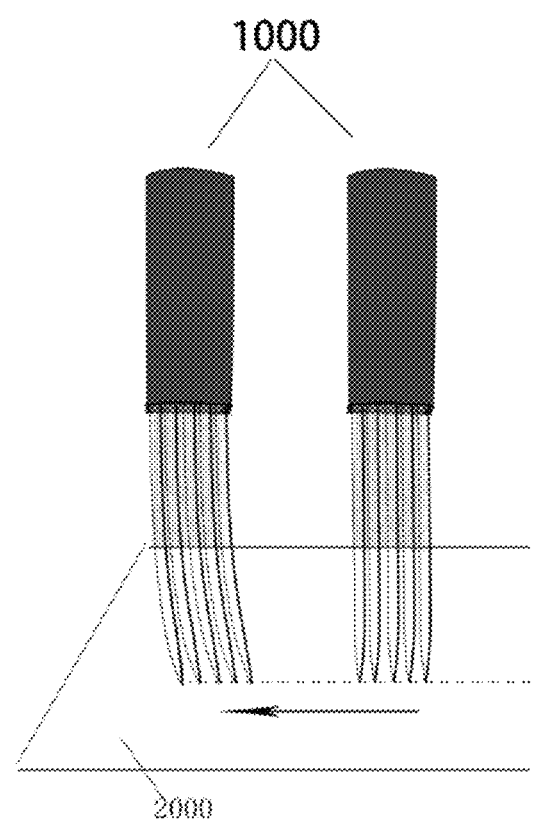
FIG. 3 is a schematic view of an in-use state of the device having multiple needles arranged in a row, as shown in FIG. 1, streaking lines to colour the skin.
Figure 4:
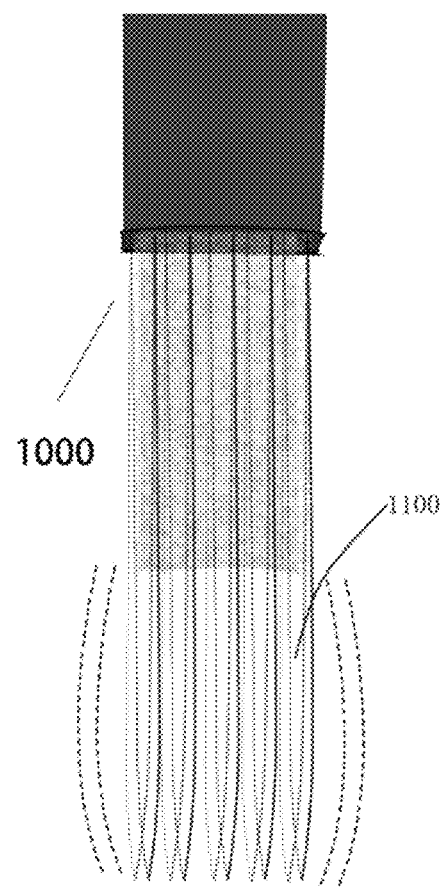
FIG. 4 is a schematic view of the device shown in FIG. 3 being elastically deformed after being used.

As shown in FIG. 3, when the device 1000 having a row of needles is streaking lines to dour the epidermis 2000, the single row of needle filaments forms a longitudinal column, successively break the skin in a direction indicated by arrows in FIG. 3, and repeatedly streak the skin. Further, when the device leaves the skin, as shown in FIG. 4, the needle filaments 1100 of the device 1000 may be elastically deformed. Therefore, the needle filaments may touch each other, resulting in the colouring pigments being splattered around.

Figure 5:
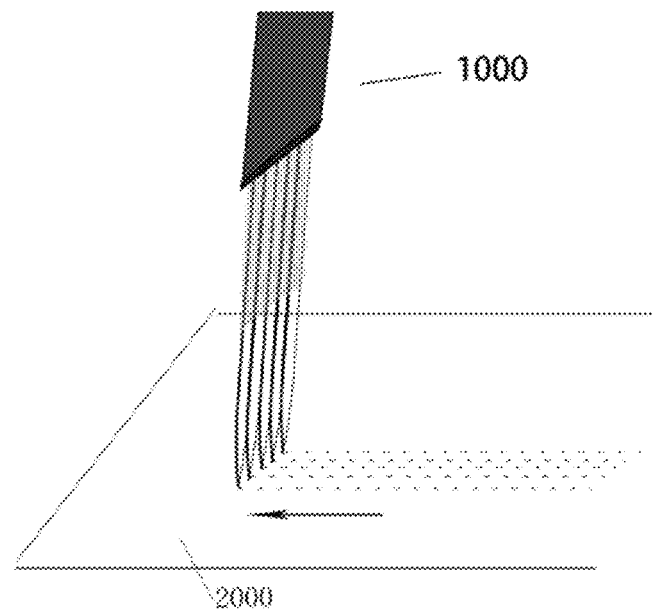
FIG. 5 is a schematic view of an in-use state of the device having multiple needles arranged in a row, as shown in FIG. 1, being used to regionally colour the skin.

As shown in FIG. 5, when the device 1000 having a row of needles does sweep to colour the epidermis 2000, the single row of needle filaments forms a horizontal column, move side-by-side at the same time in a direction indicated by arrows in FIG. 5, and repeatedly sweep the broken skin. In this case, spacings between every two adjacent needle filaments are required to be equal to each other, and the single row of needle filaments are required to pierce into the skin to reach the same depth, and only in this way, a coloured block having an even colour may be obtained.

Figure 6:
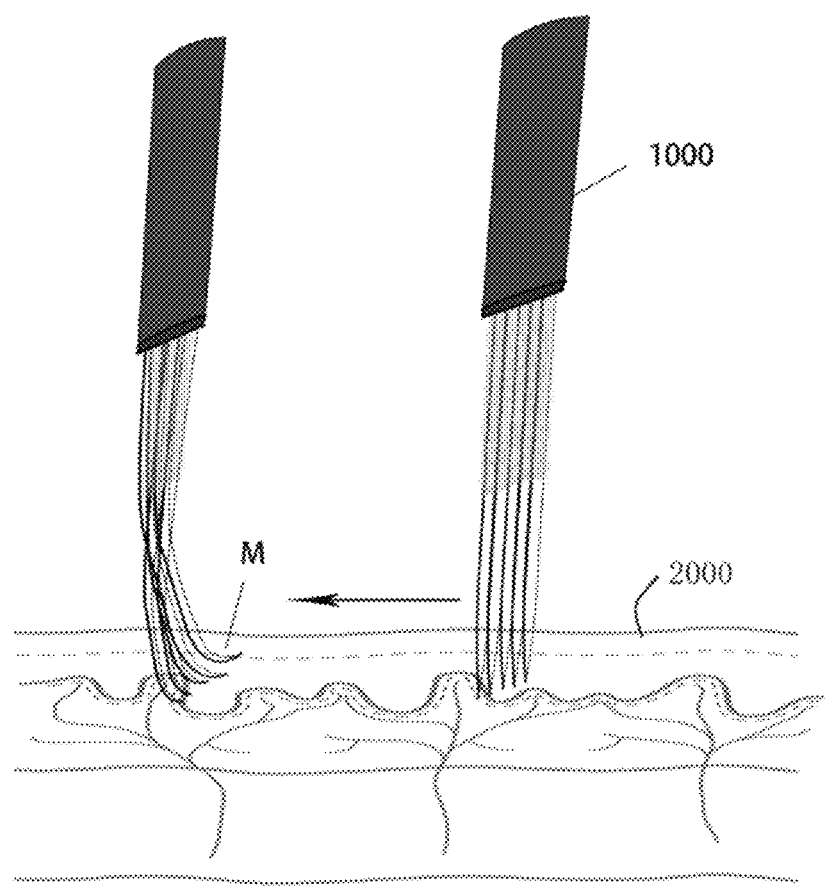
FIG. 6 is a schematic view of the device shown in FIG. 5 being elastically deformed after being used.

As shown in FIG. 6, the device 1000 having a row of needles pierces the skin and repeatedly sweeps to colour the skin. In this case, since stratum corneum of the skin has various thicknesses and toughnesses, the needle filaments of the device 1000 may be encountered by different resistance forces while moving in a direction indicated by arrows in FIG. 6. Therefore, tips M of the needle filaments may be bent to different extent, such that, when the needle filaments pierces into the skin again, spacings between adjacent needle filaments may be changed, and the needle filaments may pierce into the skin to reach different depths. Therefore, the skin may be damaged and may be coloured unevenly.

Therefore, in order to solve the deficiencies of the tattoo device in the art, the present disclosure provides a tattoo needle, which has a better colouring effect than the tattoo needle in the art.

Embodiment 1

Figure 7A:
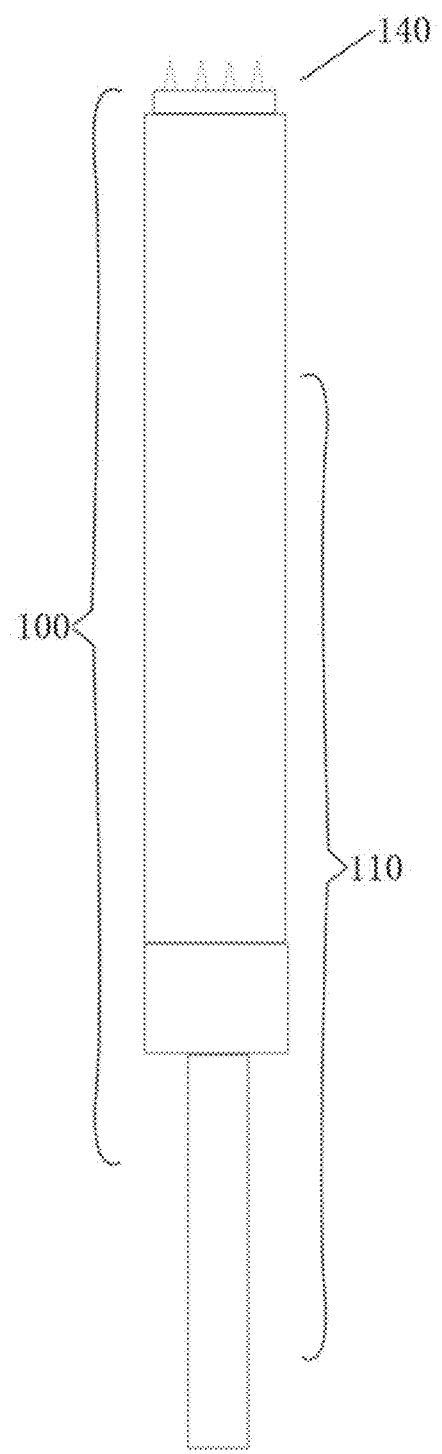
FIG. 7(a) is a structural schematic view of a tattoo needle according to an embodiment of the present disclosure.
Figure 7B:
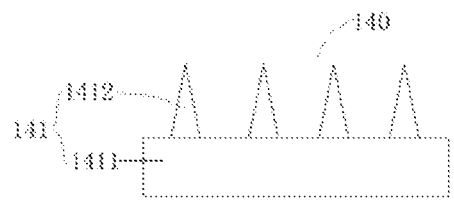
FIG. 7(b) is a structural schematic view of the needle piercing portion according to an embodiment of the present disclosure.
Figure 7C:
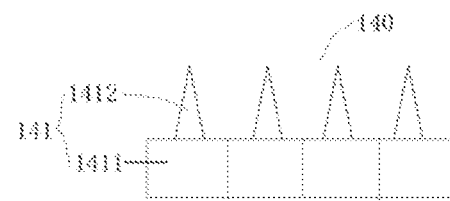
FIG. 7(c) is a structural schematic view of the needle piercing portion according to another embodiment of the present disclosure.

FIG. 7(a) shows a tattoo needle 100 having a single row of needle filaments in which a piercing depth of the single row of needles piercing into the skin may be predefined accurately. The tattoo needle 100 includes a needle piercing portion 140 and a liquid guiding member 110. As shown in FIG. 7(b), in an embodiment, the needle piercing portion 140 includes a piercing projection 141. One piercing projection 141 includes four needle teeth 1412 arranged in a single row and a substrate 1411. A length that each of four needle teeth 1412 pierces into the skin may be predefined. The four needle teeth 1412 are arranged on the substrate 1411. The substrate 1411 limits the piercing depth that the needle teeth 1412 can pierce into the skin. The substrate 1411 and the four needle teeth 1412 are configured as a one-piece and integral structure. As shown in FIG. 7(c), in another embodiment, the needle piercing portion 140 includes four piercing projections 141. Each of the four piercing projections 141 may include a needle tooth 1412 and a substrate 1411. A length that the needle tooth 1412 pierces into the skin may be predefined. The needle tooth 1412 is arranged on the substrate 1411. The substrate 1411 limits the piercing depth that the needle tooth 1412 can pierce into the skin. The substrate 1411 and the needle tooth 1412 are configured as a one-piece and integral structure.

Figure 7D:
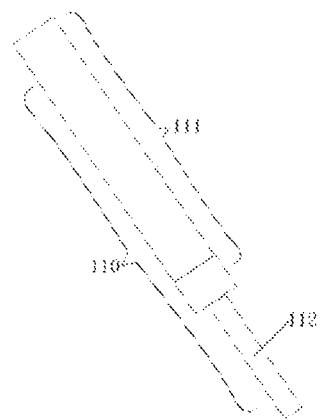
FIG. 7(d) is a structural schematic view of a liquid guiding member according to an embodiment of the present disclosure.
Figure 7E:
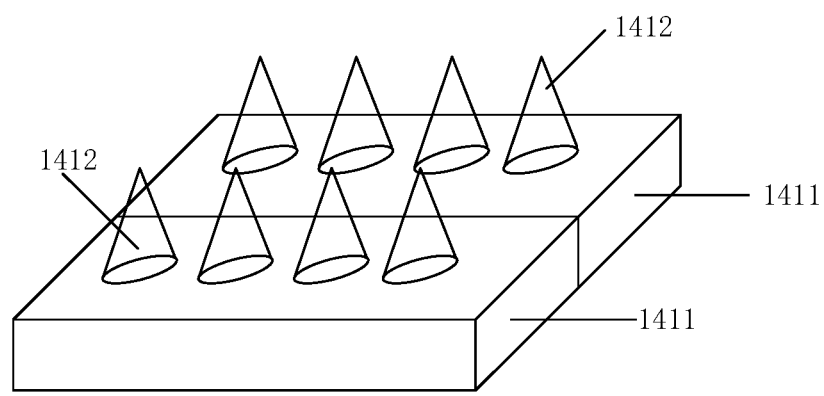
FIG. 7(e) is a structural schematic view of the needle piercing portion according to another embodiment of the present disclosure.

As shown in FIG. 7(d), the liquid guiding member 110 is a strip, including a liquid guiding post 111 and a connecting rod 112. The liquid guiding post 111 is a column, an upper portion and a lower portion of the liquid guiding post 111 are equal sized. The liquid guiding post 111 and the connecting rod 112 are connected and fixed with each other to form a one-piece component. The liquid guiding post 111 is fixedly connected to the piercing projection 141. The connecting rod 112 is connected to the tattooing rod for operation. An operator may directly hold the connecting rod for operation.

Figure 8:
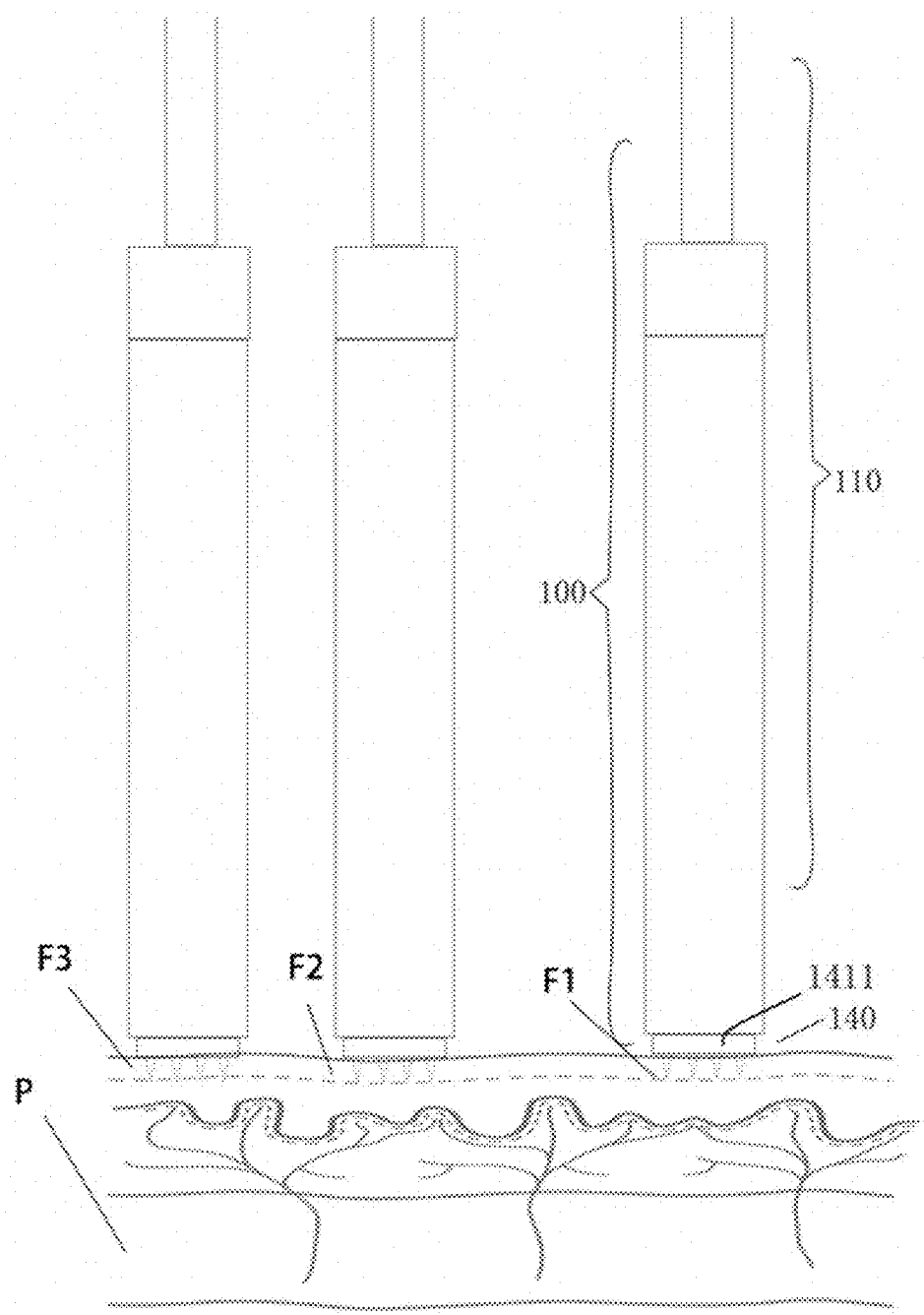
FIG. 8 shows a cross-sectional view of the tattoo needle piercing into the skin according to an embodiment of the present disclosure.

FIG. 8 shows a cross-sectional view of the tattoo needle in the present disclosure being used to pierces into the skin. The tattoo needle includes a single row of needles 100, and a piercing depth when the needles 100 pierce into the skin may be accurately limited in advance. When the tattoo needle pierces and colours the skin P, the substrate 1411 limit the piercing depth of the needles 100 piercing into the skin. In this way, depths F1, F2, and F3 reached by the needles 100 piercing into the skin in various times may be the same.

Figure 9:
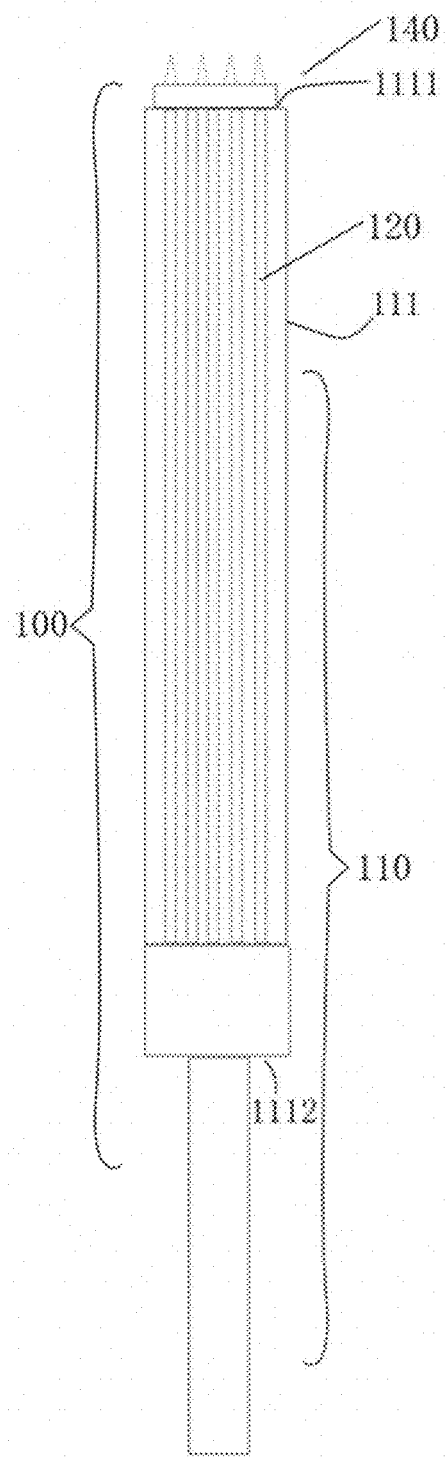
FIG. 9 is a structural schematic view of a tattoo needle according to an embodiment of the present disclosure.
Figure 10A:
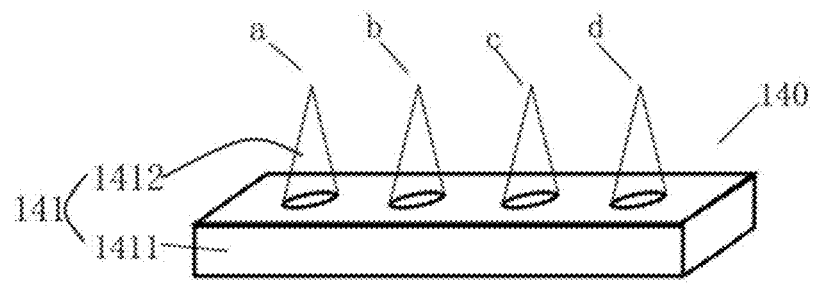
FIG. 10(a) is a structural schematic view of the needle piercing portion according to an embodiment of the present disclosure.
Figure 10B:
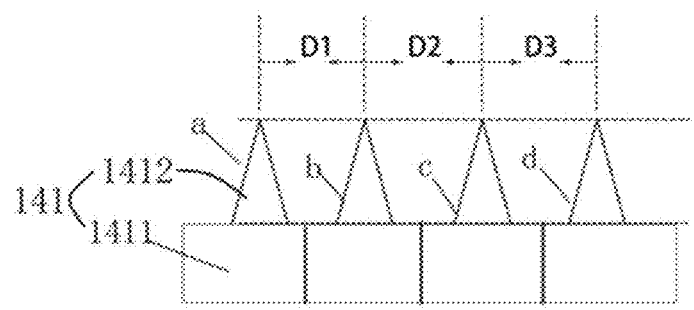
FIG. 10(b) is a cross-sectional view of the needle piercing portion according to an embodiment of the present disclosure, viewed from a viewing angle.
Figure 10C:
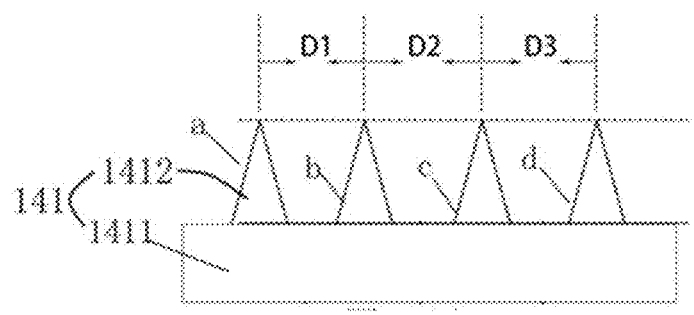
FIG. 10(c) is a cross-sectional view of the needle piercing portion according to another embodiment of the present disclosure, viewed from a viewing angle.

As shown in FIG. 9, the tattoo needle in FIG. 9 includes a needle piercing portion 140, a liquid guiding member 110, and a capillary liquid storage unit 120 arranged on an outer wall of the liquid guiding member 110. As shown in FIG. 10(a), the piercing projection 141 includes four needle teeth 1412 and a substrate 1412. A length that each of four needle teeth 1412 pierces into the skin may be predefined. The four needle teeth 1412 are arranged on the substrate 1411. As shown in the drawings, each of four needle teeth 1412 is a protrusion protruding from the substrate 1411. A size of a cross sectional area of the protrusion decreases along a direction that the needle teeth piece into the skin. For example, the size of the cross-sectional area of the protrusion decreases in a direction from the substrate 1411 towards a free end of the protrusion. The substrate 1411 and the four needle teeth a, b, c, d are configured as a one-piece and integral structure. The substrate 1411 limits the piercing depth that each of four needle teeth 1412 pierces into the skin. As shown in FIG. 10(b), the piercing projection 141 includes four needle teeth 1412 and the substrate 1412. The length that each of four needle teeth 1412 pierces into the skin may be predefined. The four needle teeth 1412 are arranged on the substrate 1411. FIG. 10(c) shows a cross-sectional view of the needle piercing portion in an embodiment. The four needle teeth a, b, c, and d have a same height and are spaced apart from each other with equal spacing. A center spacing between the needle tooth a and the needle tooth b is D1, a center spacing between the needle tooth and the needle tooth c is D2, a center spacing between the needle tooth c and the needle tooth d is D3, and D1=D2=D3. The D1 is greater than 0 less than 1500 μm. The center spacing refers to a distance between a tip end of one needle tooth to a tip end of an adjacent needle tooth. It will be understood that, in other embodiments, the four needle teeth a, b, c, and d may have different heights and are non-equally spaced apart from each other.

Figure 10D:
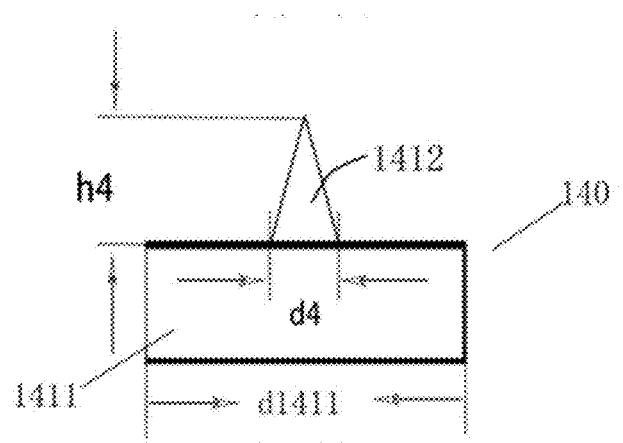
FIG. 10(d) is a cross-sectional view of the needle piercing portion according to an embodiment of the present disclosure, viewed from another viewing angle.

FIG. 10(d) shows a cross-sectional view of a short edge of the substrate on which the piercing projection is arranged. As shown in FIG. 10(d), a diameter of a bottom of the needle tooth of any piercing projection is d4, and a height of the needle tooth of any piercing projection is h4. Based on repeated experiments, in order to achieve a better effect of guiding the colour pigments, 50 μm≤h4≤1500 μm, 50 μm≤d4≤twice the height of the needle tooth, and d4<h4.

As shown in FIG. 10(d), in an embodiment, the substrate 1411 of the present disclosure may be in any polygonal shape. The needle teeth 1412 may be arranged on a side surface of the substrate 1411. In order to obtain the better effect of guiding the colour pigments, a length of the shortest edge of the substrate 1411 is recorded as d1411, when d1411>d4, the better effect of guiding the colour pigments may be achieved. Based on this configuration, the colour pigments may flow from the thicker liquid guiding post 111 to the substrate 1411 and further flow from the substrate 1411 to the needle teeth 1412.

Figure 11A:
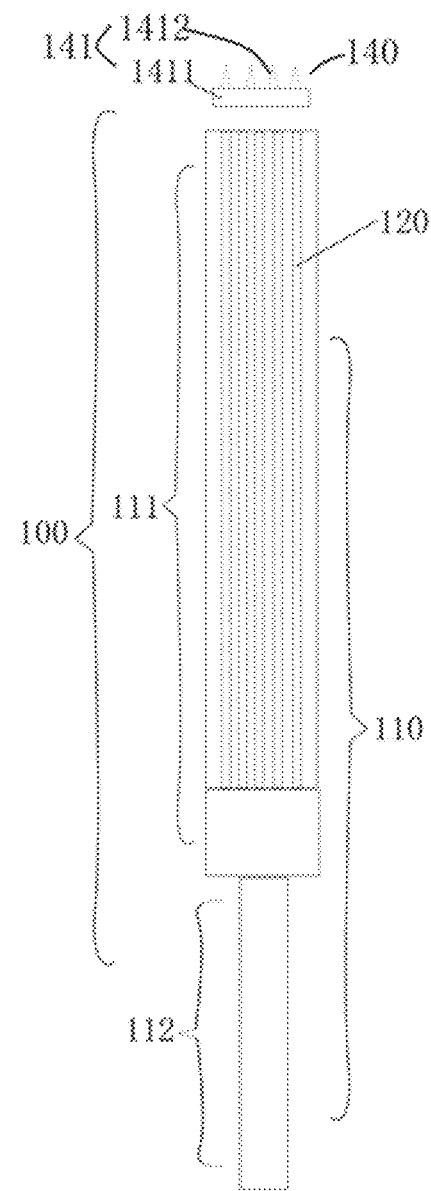
FIG. 11(a) is an exploded view of the tattoo needle according to an embodiment of the present disclosure.

As shown in FIG. 11(a), the liquid guiding member 110 is a strip and includes a liquid guiding post 111 and a connecting rod 112. The liquid guiding post 111 is disposed near the piercing projection 141. The liquid guiding post 111 may have an upper section and a lower section, and the upper section and the lower section are equal sized. The liquid guiding post 111 and the connecting rod 112 are fixedly connected with each other. The liquid guiding post 111 may be adhered to and fixed to the substrate 1411 of the piercing projection 141.

Figure 11B:
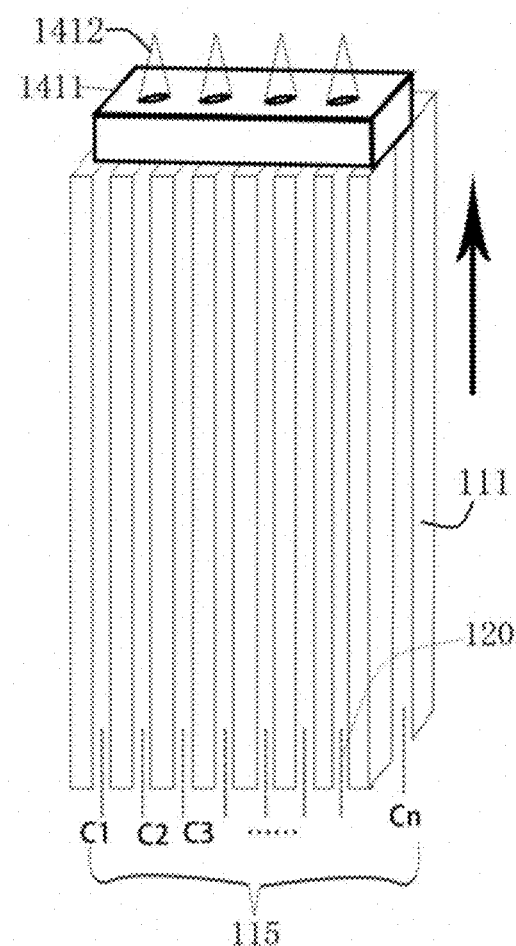
FIG. 11(b) is a perspective view of the tattoo needle according to an embodiment of the present disclosure, viewed from a viewing angle.

As shown in FIG. 11(b), the outer wall of the liquid guiding member 110 defines a plurality of channels C1, C2, C3, and Cn. A capillary liquid storage space of the plurality of channels 115 serves as the capillary liquid storage unit 120. Each of the plurality of channels C1, C2, C3, and Cn, is configured to guide the colour pigments to guide to flow to the piercing projection 141 in a direction as shown by the arrows in FIG. 11(b).

Figure 12A:
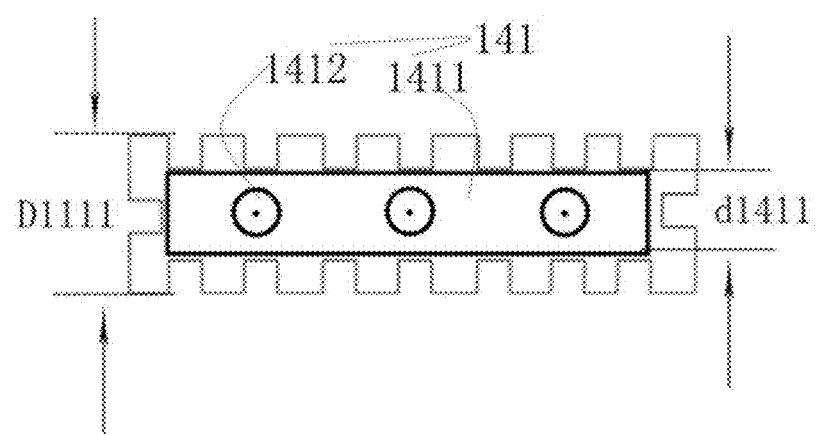
FIG. 12(a) is a planar schematic view of the tattoo needle described according to an embodiment of the present disclosure.
Figure 12B:
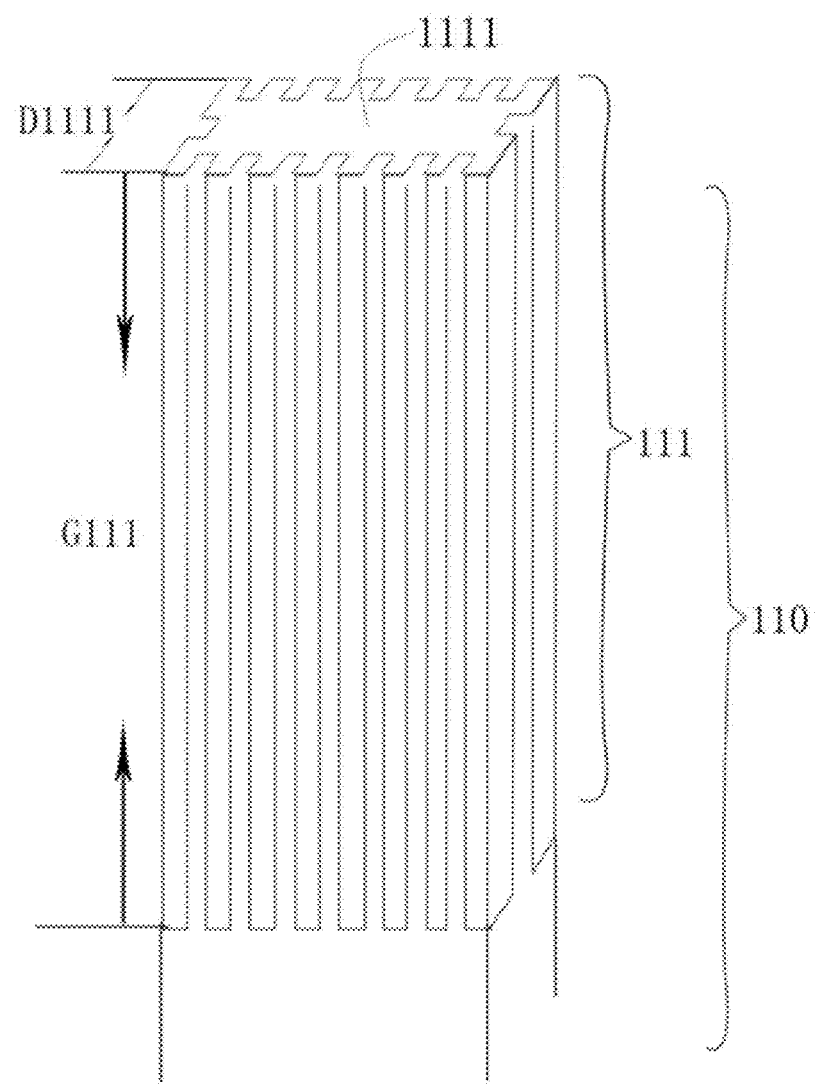
FIG. 12(b) is a perspective view of a liquid guiding member described according to an embodiment of the present disclosure.

As shown in FIG. 12(a) and FIG. 12(b), the length of the short edge of the substrate 1411 on which the piercing projection 141 is arranged is noted as d1411, the height of the liquid guiding post 111 of the liquid guiding member 110 is noted as G111, and the length of the shortest edge of the first end face 1111 of the liquid guiding post 111 is noted as D1111. Based on repeated experiments, in order to have a certain rigidity, 180 μm≤D1111≤1800 μm. In order to obtain the better effect of guiding the colour pigments, D1111≥d1411. In the present embodiment, in order to allow an increased amount of ink to be carried and to allow the ink to be released continuously and slowly, G111>2×D111, and that is, the height G111 of the liquid guiding post 111 is greater than two times of the length D1111 of the shortest edge of the liquid guiding member 110 near the piercing projection 141. Of course, a cross section of the piercing projection 141, taken by the substrate 1411, may be arbitrary polygonal, for example, the cross section may be triangular, quadrilateral, pentagonal, or in other regular or irregular polygonal shapes. When the shape of the substrate 1411 is arbitrary polygonal, an axial length of the liquid guiding post 111 is at least two times of the length of the shortest edge of the first end face 1111 of the liquid guiding post 111, and the axial length of the liquid guiding post 111 is greater than the length of the longest edge of the first end face 1111. In an embodiment, each of the plurality of channels (115) extends vertically or spirally from the first end face (1111) to the second end face. An end of each of the plurality of channels (115) may extend through or approach the second end face (1112). Each of the plurality of channels (115) may extend vertically along the liquid guiding post (111) to reach the first end face (1111). Each of the plurality of channels (115) may be an annular groove defined in the outer wall of the liquid guiding post (111), and the plurality of annular grooves are spaced apart from each other and are defined in the outer wall of the liquid guiding post (111).

Figure 13A:
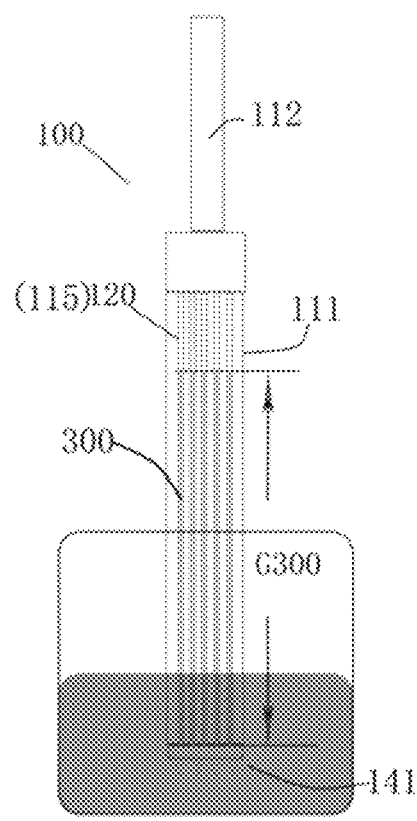
FIG. 13(a) is a schematic view of an in-use state of the tattoo needle absorbing ink according to an embodiment of the present disclosure.
Figure 13B:
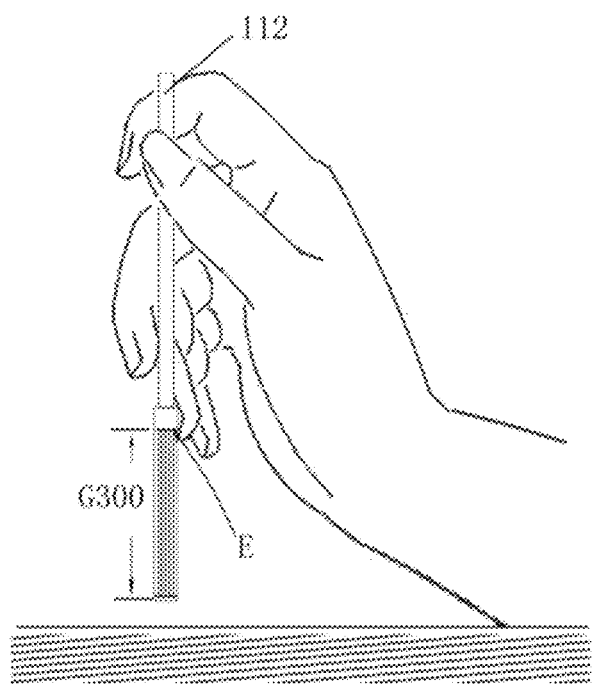
FIG. 13(b) is a schematic view of an in-use state of the tattoo needle in FIG. 13(a) piercing into the skin, after the absorbing ink, according to an embodiment of the present disclosure.

As shown in FIG. 13(*a*), when the tattoo needle 100 is dipped into and intakes the colour pigments (the colour pigments and the ink in the present disclosure refer to dyes that can colour the skin), the capillary liquid storage unit 120 arranged on the tattoo needle 100 absorbs the colour pigments based on a capillarity absorption principle and temporarily stores colour pigments.

The colour pigments rises up along the channels of the capillary liquid storage unit 120 to form a pigment column, recorded as G300. By collecting and analyzing data, a density of the pigments in the art at room temperature is about 0.7-1.31 g/ml, and a surface tension of the pigments at the room temperature is almost equal to a surface tension of water, which is about 72 mN/m. A capillary formula is as follows: a height h that the liquid rises along a capillary tube=2*surface tension coefficient*cos θ/(density of the liquid*gravitational acceleration g*radius of the capillary tube r). The θ is an angle between a liquid surface and a wall of the capillary tube. The radius of the channel of the liquid storage unit 120 (or the depth and/or width of the channel) corresponds to the radius of the capillary tube r in the capillary formula. According to the experimental test and verification of the capillary formula, as the radius (or the depth and/or the width) of the channel of the capillary liquid storage unit 120 is reduced, the G300 is increased. That is, as the channel of the capillary liquid storage unit 120 is thinner, the height of the pigment column is higher, and more pigments may be carried. Therefore, the needle may not dip the pigments frequently, the tattooing may be performed continuously and efficiently. In the present embodiment, the liquid guiding member 110 of the tattoo needle 100 is made of plastics. Based on precision of the main production process in the art, the radius of the channel of the capillary liquid storage unit 120 may be made to have a precision of 0.1 mm, and the height of the pigment column G300 may be more than 100 mm. However, as shown in FIG. 13(*b*), according to a conventional way that the operator holds the tattoo needle 100 by hand and a measurement of dimensions of a general human hand, a lowest position E of the tattoo needle 100 that is held by the hand is generally not more than 50 mm from the needle tip. Therefore, the height of the channel of the capillary liquid storage unit 120 arranged on the tattoo needle 100 in the present embodiment is <50 mm.

Figure 14A:
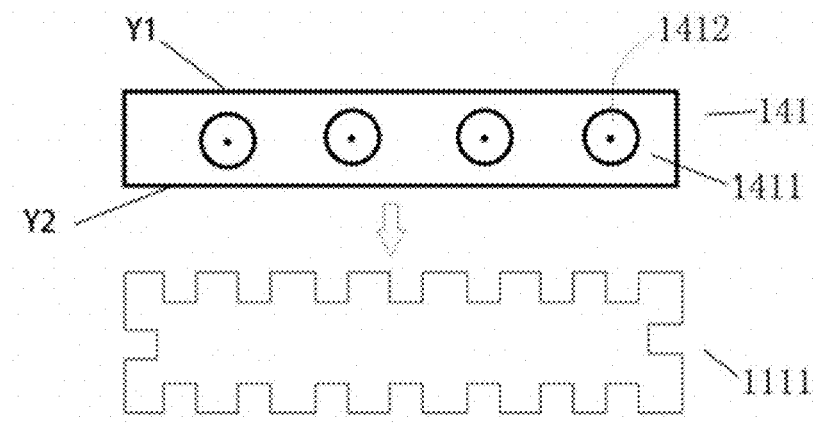
FIG. 14(a) is a schematic view of the needle piercing portion being mounted with the liquid guiding post according to an embodiment of the present disclosure.
Figure 14B:
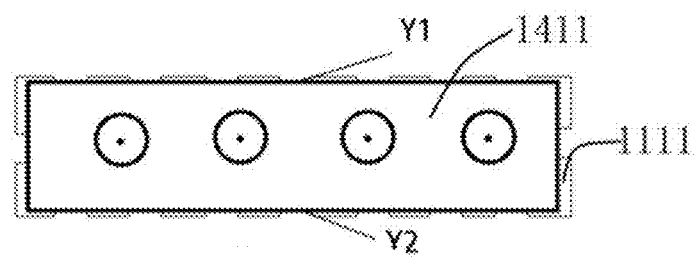
FIG. 14(b) is a schematic view of the substrate being mounted with the liquid guiding post according to an embodiment of the present disclosure.
Figure 14C:
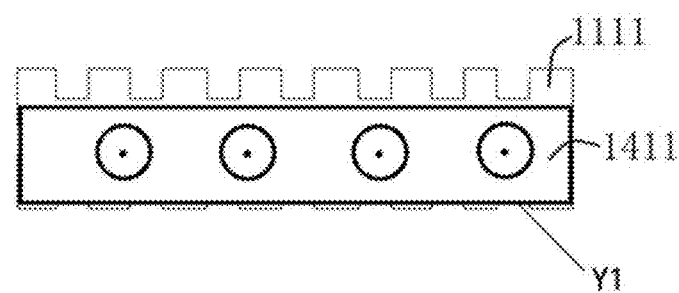
FIG. 14(c) is a schematic view of the substrate being mounted with the liquid guiding post according to another embodiment of the present disclosure.

As shown in FIG. 14(*a*), the piercing projection 141 may be adhered on the first end face 1111 of the liquid guiding post, obtaining structures shown in FIG. 14(*b*) and FIG. 14(*c*). In order to achieve the better effect of guiding the colour pigment, at least one side (Y1, Y2) of the substrate 1411 on which the piercing projection 141 is arranged is aligned (or infinitely approach) with an edge of an outer wall of the first end face 1111 of the liquid guiding member 110.

In an embodiment, at least one substrate 1411 of the piercing projection 141 is disposed at a middle of an end face of the liquid guiding member 110, and a distance from the edge of the outer wall of the liquid guiding member to one corner or one edge of the substrate is not more than 0.18 mm. That is, in an embodiment, the substrate may be disposed at a center of the first end face. However, in order to achieve the better effect of guiding the pigments, a distance from the edge of the outer wall of the liquid guiding member to one corner or one edge of the substrate is not more than 0.18 mm.

Figure 15:
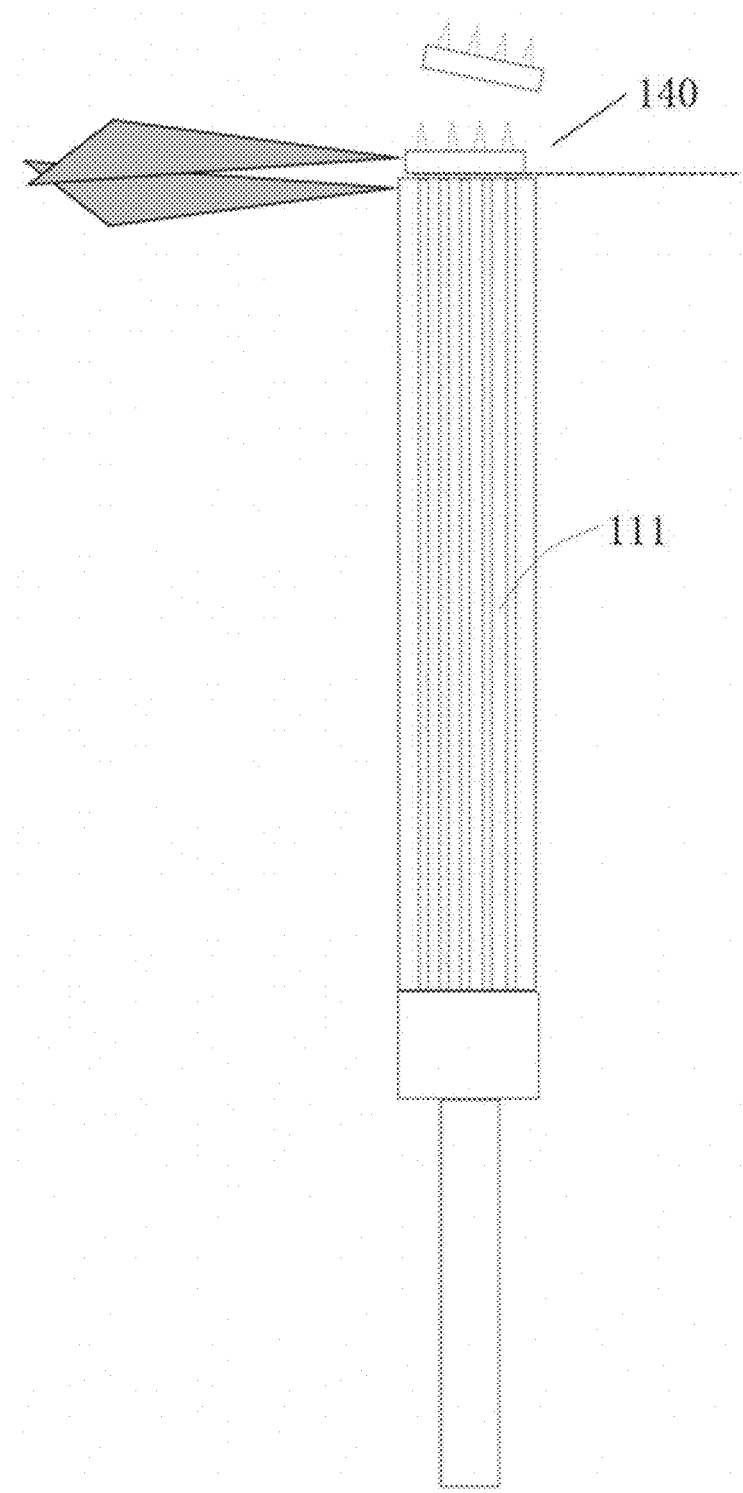
FIG. 15 is a schematic view of a state of destroying a used tattoo needle according to an embodiment of the present disclosure.

As shown in FIG. 15, for the tattoo needle 100 in the present embodiment, an adhesive seam is defined between the liquid guiding member 110 and the piercing projection 141. After use, the tattoo needle 100 may be functionally destroyed by separating, by any sharp instrument, the liquid guiding member 110 from the piercing projection 141.

Embodiment 2

Figure 16A:
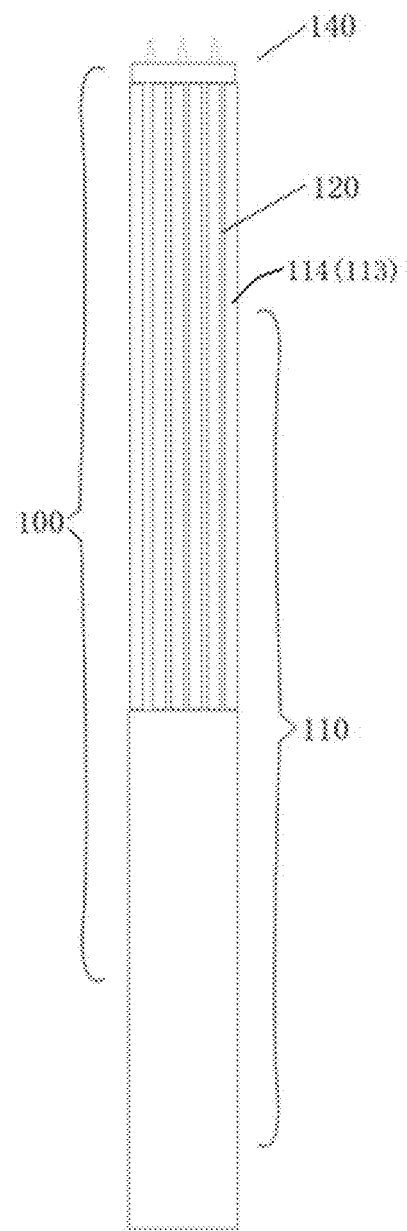
FIG. 16(a) is a schematic view of a tattoo needle according to an embodiment of the present disclosure.
Figure 16B:
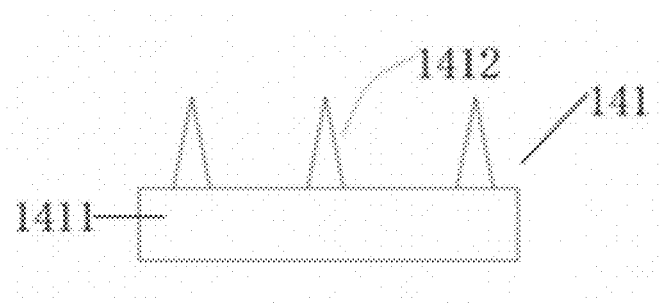
FIG. 16(b) is a schematic view of the needle piercing portion in FIG. 16(a).
Figure 16C:
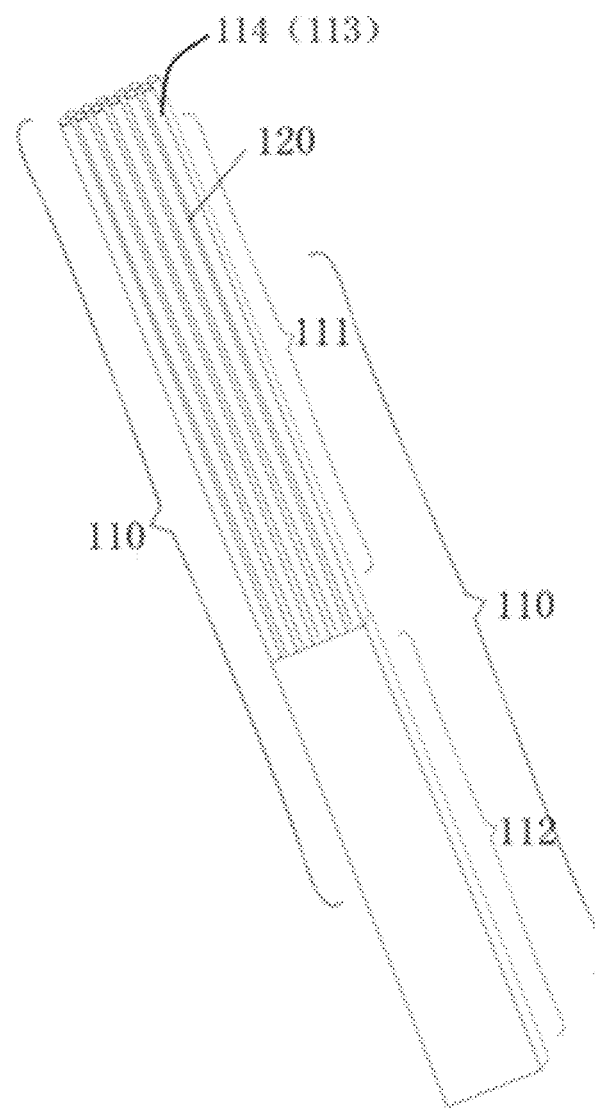
FIG. 16(c) is a schematic view of the liquid guiding member in FIG. 16(a).

In an embodiment, FIG. 16(*a*) shows a tattoo needle 100 having a single row of needles, and the piercing depth that the needles pierce into the skin can be predefined accurately. The tattoo needle 100 includes a piercing projection 141, a liquid guiding member 110, and a capillary liquid storage unit 120.

As shown in FIG. 16(*b*), the piercing projection 141 includes three needle teeth and one substrate 1411. The piercing depth that the three needle teeth pierce into the skin is predefined, and the three needle teeth 1412 are arranged on the substrate 1411. Each of the three needle teeth 1412 is a protrusion protruding from the substrate 1411. A size of a cross sectional area of the protrusion decreases along a direction that the needle teeth piece into the skin. For example, the size of the cross-sectional area of the protrusion decreases in a direction from the substrate 1411 towards a free end of the protrusion. For example, the needle tooth may be tower-shaped, conical, or the like. FIG. 16(*b*) shows conical needle teeth. The substrate 1411 and the three needle teeth are configured as a one-piece and integral structure. The substrate 1411 limits the piercing depths that the three needle teeth pierce into the skin.

As shown in FIG. 16(*c*), the liquid guiding member 110 is a strip and includes a liquid guiding post 111 and a connecting rod 112. The liquid guiding post 111 is disposed near the piercing projection 141. The liquid guiding post 111 may have an upper section and a lower section, and the upper section and the lower section are equal sized. The liquid guiding post 111 includes twelve metal filaments, each of the twelve metal filaments has a flat-cut end (the filaments in the drawings are only schematic to show one configuration of the liquid guiding post, and the filaments may alternatively be referred to as flat-end needle filaments 113 or small posts 114), C1, C2, C3, and C12. The twelve metal filaments, C1, C2, C3, and C12, may be adjacent to each other and are not fixedly connected with each other. A gap between the twelve metal filaments may have the capillary effect and serves as the capillary liquid storage unit 120. The liquid guiding post 111 and the connecting rod 112 are fixedly welded with each other.

Figure 17A:
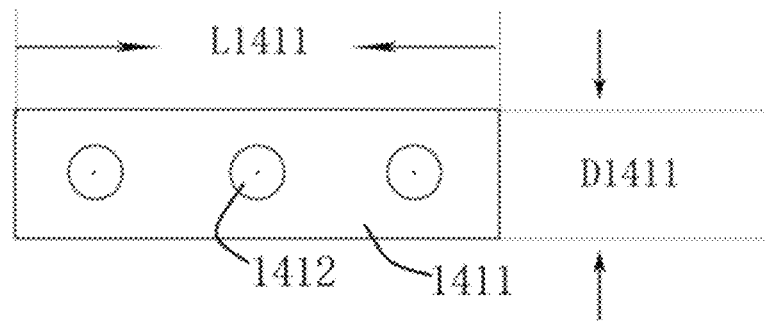
FIG. 17(a) is a planar schematic view of the needle piercing portion according to an embodiment of the present disclosure, viewed from a viewing angle.
Figure 17B:
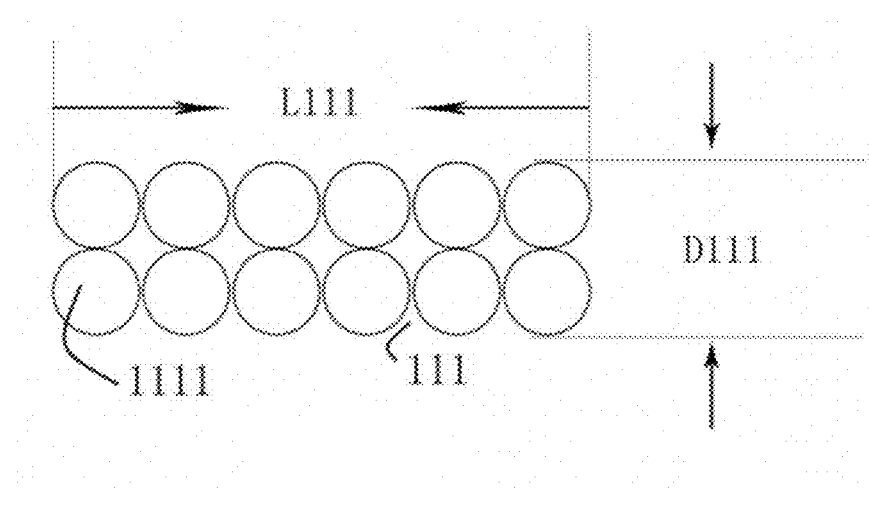
FIG. 17(b) is a cross-sectional view of the liquid guiding post (referred to as a planar schematic view of the first end face of the liquid guiding post) according to an embodiment of the present disclosure.

As shown in FIG. 17(*a*) and FIG. 17(*b*), in order to obtain the better effect of guiding the colour pigments, a longer edge L1411 of the cross section of the substrate 1411 is shorter than or equal to a longer edge L111 of the first end face 1111 of the liquid guiding member 111, and that is, L1411≤L111. The shorter edge D1411 of the cross section of the substrate 1411 is shorter than or equal to the shorter edge D1111 of the first end face 1111 of the liquid guiding member 111.

As shown in FIG. 18(*a*) and FIG. 18(*b*), one longer edge P1 of the substrate 1411 of the piercing projection 141 is aligned (infinitely approach) with the edge of the outer wall of the liquid guiding post 111. Alternatively, as shown in FIG. 18(*b*), two longer edges M1, M2 of the substrate 1411 of the piercing projection 141 are aligned (infinitely approach) with the edge of the outer wall of the liquid guiding post 111.

Figure 19:
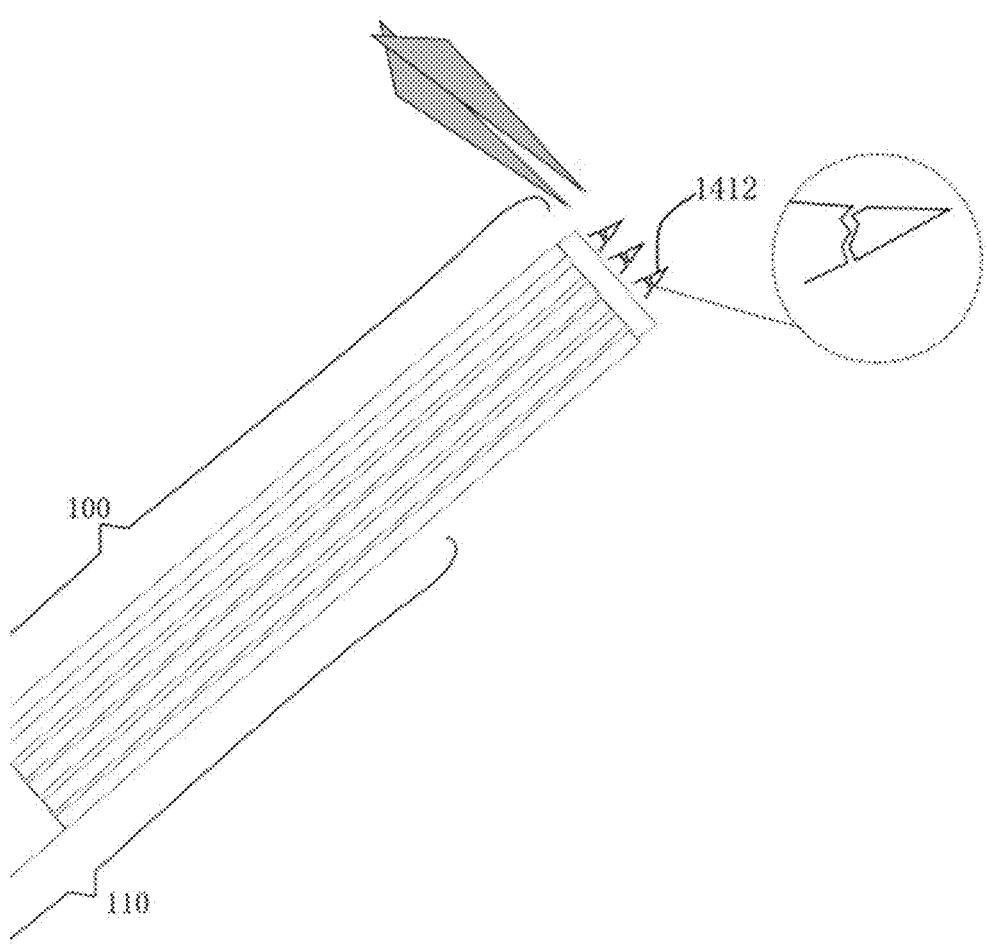
FIG. 19 is a schematic view of a state of destroying a used tattoo needle according to an embodiment of the present disclosure.

As shown in FIG. 19, for the tattoo needle 100 in the present embodiment, the liquid guiding member 110 and the piercing projection 141 are welded and fixed with each other. The piercing projection 141 may be made of monocrystalline silicon. The tattoo needle 100 may be functionally destroyed by using a sharp instrument to knock off the needle teeth.

Embodiment 3

Figure 20A:
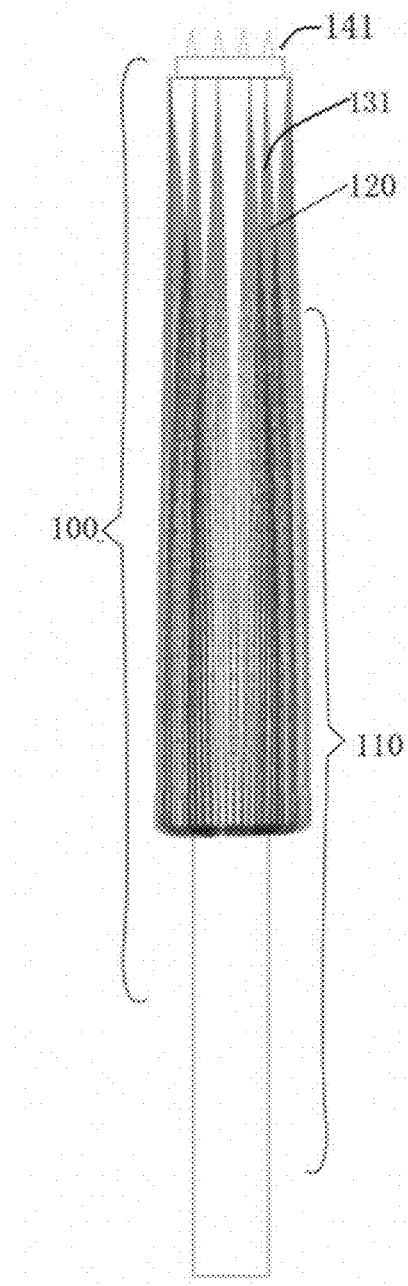
FIG. 20(a) is a schematic view of the tattoo needle according to an embodiment of the present disclosure.

In an embodiment, FIG. 20(a) shows a tattoo needle 100 having a single row of needles, and the piercing depth that the needles pierce into the skin can be predefined accurately. The tattoo needle 100 includes a piercing projection 141, a liquid guiding member 110, and a capillary liquid storage unit 120.

Figure 20B:
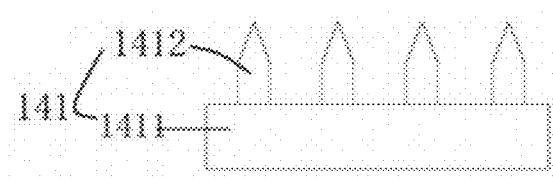
FIG. 20(b) is a cross-sectional view of the needle piercing portion in FIG. 20(a).
Figure 20C:
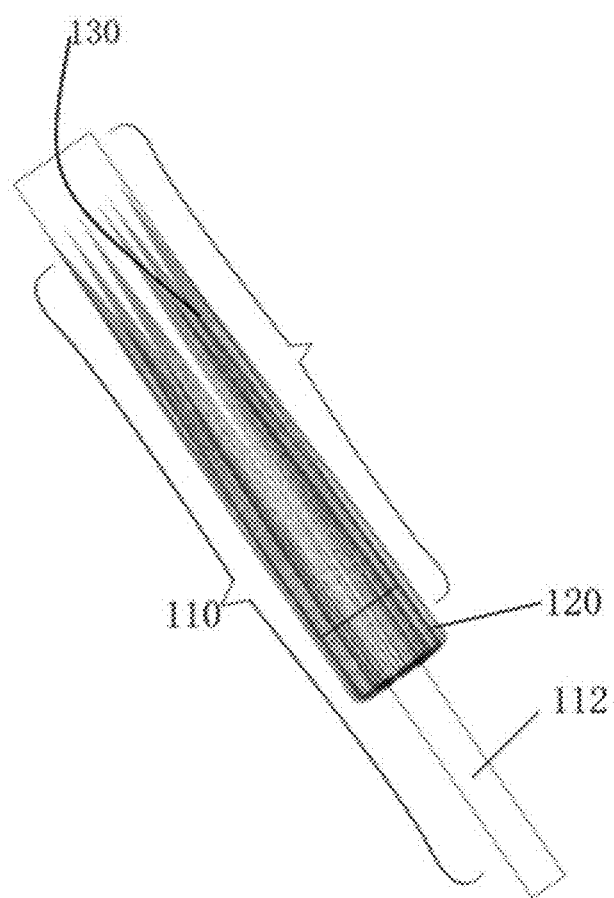
FIG. 20(c) is a schematic view of the liquid guiding member in FIG. 20(a).

The liquid guiding member 110 is fixed with the piercing projection 141. As shown in FIG. 20(b), the piercing projection 141 includes four needle teeth and a substrate 1411. The length that each of the four needle teeth pierces into the skin may be predefined, and the four needle teeth are arranged on the substrate 1411. Each of the four needle teeth includes a tail pin and a top pin integrally formed with an end of the tail pin. The tail pin is columnar, and the top pin is protruding from the tail pin. A size of a cross sectional area of the top pin decreases in a direction extending from the tail pin to a free end of the top pin away from the tail pin, and the other end of the columnar tail pin is fixedly connected to the substrate. For example, the needle tooth may be tower shaped, and the substrate 1411 and the four needle teeth are configured as a one-piece and integral structure. The substrate 1411 limits the piercing depth that the four needle teeth pierce into the skin. As shown in FIG. 20(c), in an embodiment, the liquid guiding member 110 is a strip and includes a liquid guiding post 111 and a connecting rod 112. A portion of the liquid guiding post 111 near the piercing projection 141 is columnar. A fibrous substance is attached to the outer wall or a side of the liquid guiding post 111. A gap inherently included in the fibrous substance and a gap between the fibrous substance and the outer wall of the liquid guiding post 111 serve as the capillary liquid storage unit 120.

Embodiment 4

As shown in FIG. 7(a) to FIG. 7(d), in an embodiment, a tattoo needle in the present embodiment includes a liquid guiding member 110 and a needle piercing portion 140 disposed at an end of the liquid guiding member 110. The needle piercing portion 140 includes at least one piercing projection 141. Each piercing projection 141 includes a substrate 1411 and a needle tooth 1412. The needle tooth 1412 is fixedly arranged on a side surface of the substrate 1411. A central axis of the needle tooth 1412 is perpendicular to the side surface of the substrate 1411. When the needle is piercing the skin, the substrate 1411 may limit a piercing depth that the needle pierces the skin. The substrate 1411 presses against the skin to limit the piercing depth that the needle tooth 1412 pierces into the skin. The needle piercing portion shown in FIG. 7(b) includes one piercing projection 141, and the piercing projection 141 includes one substrate 1411 and four needle teeth 1412 arranged on the substrate 1411. The needle piercing portion shown in FIG. 7(c) includes four piercing projections 141. Each of the four piercing projections 141 includes one substrate 1411 and one needle tooth 1412 arranged on the substrate 1411 (or a plurality of needle teeth on the substrate 1411, FIG. 7(c) shows one needle tooth arranged on the substrate). The liquid guiding member 110 may be columnar. The other side surface of the substrate 1411 is fixed to an end of the columnar liquid guiding member 110. A central axis of the columnar liquid guiding member 110 is parallel to the central axis of the needle tooth 1412. The structure of the tattoo needle 100 may be similar to a pen. The liquid guiding member 110 may be similar to a barrel of the pen. The needle piercing portion 140 may be similar to a tip of the pen. The liquid guiding member 110 may pierce the skin in the vertical direction, ensuring that a piercing position may not be shifted, the needle tip may not slip, and a redundant wound may not be generated.

As shown in FIG. 7(a) to FIG. 7(d), in an embodiment, the liquid guiding member 110 may include a liquid guiding post 111 and a connecting rod 112 connected to the liquid guiding post 111. That is, the liquid guiding member 110 includes two parts, one of the two parts guides ink to flow, and the other one of the two parts is configured for connection and driving. The connecting rod 112 is connected to a drive portion. The liquid guiding member 110 reciprocates, driven by the drive portion, along the central axis of the liquid guiding member 110. In a case, the drive portion may be a motorized rod, and that is, the connecting rod 112 of the liquid guiding member 110 is directly connected to the motorized rod (which may be fixed connection or a non-fixed connection (including abutting connection, hanging connection, and contact connection)). The motorized rod directly drives the liquid guiding member 110 to move. In another case, the drive portion may be an elastic member 170, such as a spring. The connecting rod 112 of the liquid guiding member 110 is connected to an end of the spring. A case (or a member fixedly connected to the case) is connected to the other end of the spring. Further, an external force is applied to drive the spring to be deformed. When the liquid guiding member 110 is moving along an axial direction of the case 150 towards a needle outlet end, the liquid guiding member 110 may be reset by a force from the deformed elastic member, such that the liquid guiding member 110 moves reciprocately within the case 150. In still another case, an operator may also hold the connecting rod 112 by hand to directly tattoo.

In order to achieve various tattoo patterns and tattoo positions, the present embodiment provides a piercing projection 141, as shown in FIG. 7(b). The piercing projection 141 may include one substrate 1411 and four needle teeth 1412 arranged on the substrate 1411. The substrate 1411 serves as a depth limiting plate to limit the piercing depth that the four needle teeth 1412 pierce into the skin. The substrate 1411 and the four needle teeth 1412 may be configured as a one-piece and integral structure, or configured as separated elements being fixedly connected with each other. When the substrate 1411 and the four needle teeth 1412 are configured as the one-piece and integral structure, connection strength and stability of the needle teeth 1412 may be enhanced. Further, safety of the needle teeth 1412 may be improved while the needle teeth 1412 are piercing the skin. The one-piece and integral structure may be suitable for a high frequency piercing process.

Advantages of the tattoo needle in the present disclosure, compared to the device that has a row of needles in the art, will be illustrated below by referring to FIG. 6 and FIG. 8.

As shown in FIG. 6, when the device 1000 having a row of needles pierces into the skin and repeatedly sweeps to apply colour to the skin, the needle filaments of the device 1000 encounter different resistance forces, needle tips M of the needle filaments are bent to different extent, and spacings between the needle filaments may be changed. As shown in FIG. 8, when the tattoo needle of the present disclosure is used to repeatedly sweep, streak, or prick at points to colour the skin, piercing depths that the needle teeth pierce into the skin is controllable through the substrate 1411. The needle teeth may not compress each other and may not be elastically deformed. While the tattoo needle is being used, the needle teeth may not impact each other, the piercing depths that the needle teeth pierce into the skin is controllable, and the needle teeth may not be bent. Therefore, the tattoo needle of the present disclosure has better effect and structural advantages over the device that has a row of needles in the art.

Embodiment 5

As shown in FIG. 9, in an embodiment, the liquid guiding post 111 may have a first end face 1111 and a second end face 1112. The central axis of the liquid guiding column 111 extends through a center of the first end face 1111 and a center of the second end face 1112. The liquid guiding column 111 may be a column in any shape, such as a cylinder, a quadratic column, a cone-like column, a circular truncated cone, or an irregular column, and so on. A side surface of the substrate 1411 is fixed to the first end face 1111 of the liquid guiding post 111 (the substrate may be adhered to and fixed to the first end face). The connecting rod 112 may be fixedly or detachably connected to the second end face 1112 of the liquid guiding post 111. The connecting rod 112 may be a column or in other shapes. The connecting rod 112 is substantially configured to connect the liquid guiding post 111 to the drive portion.

In an embodiment, a shape of the liquid guiding post 111 of the present disclosure may be arbitrary, as long as any one of the following conditions is met.

For a condition 1, a shape of the first end face 1111 is the same as a shape of the second end face 1112, and a size of the first end face 1111 is the same as a size of the second end face 1112.

For a condition 2, the shape of the first end face 1111 is the same as the shape of the second end face 1112, and the size of the first end face 1111 is less than the size of the second end face 1112.

For a condition 3, the shape of the first end face 1111 is different from the shape of the second end face 1112, and the size of the first end face 1111 is less than the size of the second end face 1112.

Based on the above conditions, the most basic characteristics of the liquid guiding member 110 is that the liquid guiding member 110 is a column. As long as the liquid guiding member 110, when being vertically disposed, may guide and direct liquid to flow, the shape of the liquid guiding member 110 is arbitrary. The shape of the liquid guiding member 110 may be determined based on the operator's demands. The accompanying drawings, which show that the shape is columnar and conical-like, are for illustrating the structure of the liquid guiding member only, and shall not be interpreted as limiting the shape of the shape of the liquid guiding member 110.

In an embodiment, the axial length of the liquid guiding post 111 is greater than a length of the longest edge or a diameter of a cross section of the first end face 1111 of the liquid guiding post 111. That is, the liquid guiding post 111 of the present disclosure is preferably an elongated column.

In an embodiment, the axial length of the liquid guiding post 111 is at least two times of the length of the shortest edge or the diameter of the first end face 1111 of the liquid guiding post 111, and the axial length of the liquid guiding post 111 is greater than the length of the longest edge or the diameter of the first end face 1111. When this length-to-diameter ratio is met, the shape of the liquid guiding member 110 is standardized, and the elongated liquid guiding member 110, when being vertically disposed, provides a better liquid guiding and storage effect.

Embodiment 6

In the tattoo process, the tattoo ink 300 (or dye) may be introduced into a superficial layer of the skin through the tattoo tool. The tattoo tool in the art may not adsorb, when being submerged into the ink 300, a large amount of ink 300. In a process that the tool pierces into the skin highly frequently, the amount of ink in the tattoo tool does not reach the amount of ink required for one piercing stage. Therefore, a high rate of empty needle during piercing may be caused. In order to improve the above mentioned defects of the tattoo tool in the art, the liquid guiding member 110 of the tattoo needle in the present disclosure is improved to meet the amount of ink required for one tattoo process. The structure of the liquid guiding member 110 will be described in detail below.

As shown in FIG. 11(*a*), FIG. 11(*b*), FIG. 12(*a*), FIG. 12(*b*), FIG. 13(*a*), and FIG. 13(*b*), the capillary liquid storage unit 120 is arranged in the liquid guiding post 111. The capillary liquid storage unit 120 may absorb, by resisting against the gravitational force, liquid and temporarily store the liquid. The liquid is guided (under the gravitational force or other forces) to flow to the needle piercing portion 140. The needle tooth 1412 pierces into the surface of the skin, and at the same time, the liquid is introduced into the surface of the skin along the needle tooth 1412. The capillary liquid storage unit 120 may temporarily store the ink 300. The liquid guiding member 110 may be submerged in an ink bottle, and the capillary liquid storage unit 120 in the liquid guiding member 110 may adsorb and temporarily store the ink. When the liquid guiding member 110 carries the needle tooth 1412 of the needle piercing portion 140 to pierce into the skin, the ink 300 stored in the capillary liquid storage unit 120 is gradually guided to flow to the tip of the needle tooth 1412. In the present disclosure, the capillary liquid storage unit 120 is arranged to allow the liquid guiding member 110 to release the ink gradually, ensuring continuous supply of the ink and reducing a rate of empty needles.

According to the above embodiments, the tattoo needle is required to break into the skin during the tattoo process. Therefore, the tattoo needle that has been used needs to be destroyed to prevent microbial spread caused by secondary usage. The tattoo needle provided by the present disclosure has taken this into account. Therefore, as shown in FIG. 15 and FIG. 19, the needle tooth 1412 of the tattoo needle may be destroyed. Alternatively, the needle piercing portion 140 of the tattoo needle may be directly destroyed, and the remaining liquid guiding post 111 may be further reused.

As shown in FIG. 11(*b*), in an embodiment, the liquid guiding post 111 of the present disclosure defines a plurality of channels 115. The plurality of channels 115 extend along the axial direction of the liquid guiding member 110 and are defined in the outer wall of the liquid guiding post 111 and/or at an interior of the liquid guiding post 111. The plurality of channels 115 cooperatively serve as the capillary liquid storage unit 120. The capillary liquid storage unit 120 is substantially configured to continuously supplying ink 300 to the tip of the needle tooth 1412. Therefore, at least one of the plurality of channels 115 temporarily stores the liquid, and the liquid in the at least one of the plurality of channels 115 may be guided by the gravitational force to flow to reach the needle tooth 1412 of the needle piercing portion 140. The plurality of channels 115 may be integrally defined in the outer wall of the liquid guiding member 110 by etching, cutting, engraving and grinding, or injection molding.

In an embodiment, the plurality of channels 115 are defined in the outer wall of the liquid guiding post 111. The plurality of channels 115 serve as the capillary fluid storage unit 120. The plurality of channels 115 in the present embodiment may be objects, such as a needle filament or a needle tube, that are connected to the liquid guiding post 111 and may form a gap.

As shown in FIG. 16(a) to FIG. 16(b), in an embodiment, the liquid guiding post 111 of the present disclosure may be formed by a plurality of needle filaments 113 having flat ends and/or a plurality of small posts 114. The plurality of needle filaments 113 having the flat ends and the plurality of small posts 114 are arranged adjacent to each other. Alternatively, the plurality of said needle filaments 113 having the flat ends are arranged adjacent to each other. Alternatively, the plurality of small posts 114 are arranged adjacent to each other. A gap between two adjacent needle filaments 113 having the flat ends serves as the channel 115 which serves as the capillary liquid storage unit 120. A gap between two adjacent small posts 114 serves as the channel 115 which serves as the capillary liquid storage unit 120. A gap between one needle filament 113 having the flat end and one small post 114 serves as the channel 115 which serves as the capillary liquid storage unit 120. The needle filament or the small post 114 in the present embodiment may be solid or hollow. The capillary may be formed by the gap, which is defined by splicing the needle filaments or the small posts 114. Alternatively, the needle filament or the small post 114 may be configured to be hollow to provide an auxiliary capillary.

Embodiment 7

As shown in FIG. 20(a), the capillary liquid storage unit 120 in the present disclosure may be arranged by attaching a structure to an outside of the liquid guiding post. In the present embodiment, a liquid storage structure 130 is provided and includes one or more sheets. The sheets are attached to the outer wall of the liquid guiding post 111, and a gap is defined between the outer wall of the liquid guiding post 111 and the sheets. The gap serves as the capillary liquid storage unit 120. The capillary liquid storage unit 120 stores liquid temporarily. The liquid is guided to flow to the needle tooth 1412 of the needle piercing portion 140.

In an embodiment, the liquid storage structure 130 is formed by natural or man-made porous sheets.

In another embodiment, the liquid storage structure 130 includes a plurality of filaments. The plurality of filaments includes fiber filaments 131. A gap between the plurality of fiber filaments 131 and a gap between the fiber filaments 131 and the outer wall of the liquid guiding post 111 serve as the capillary liquid storage unit 120. The capillary liquid storage unit 120 stores liquid temporarily. The liquid is guided to flow to the needle tooth 1412 of the needle piercing portion 140.

In an embodiment, the fiber filaments 131 may include animal hair, plant fiber filaments 131, chemical fiber filaments, and so on.

In an embodiment, the filaments may further include metal filaments. A gap between the metal filaments and a gap between the metal filaments and the outer wall of the liquid guiding member 110 serve as the capillary storage unit 120. The capillary storage unit 120 stores liquid temporarily, and the liquid is guided to flow to the needle tooth 1412 of the needle piercing portion 140.

In an embodiment, a position to which the liquid storage structure 130 is attached and area that the attached liquid storage structure 130 occupies may be determined based on a unit amount of ink stored in the liquid storage structure 130 and a target amount of stored ink of the liquid guiding member 110. Alternatively, the number of layers of the liquid storage structure 130 and the area of the liquid storage structure 130 may be determined based on the amount of ink used for tattoo.

Embodiment 8

Figure 18A:
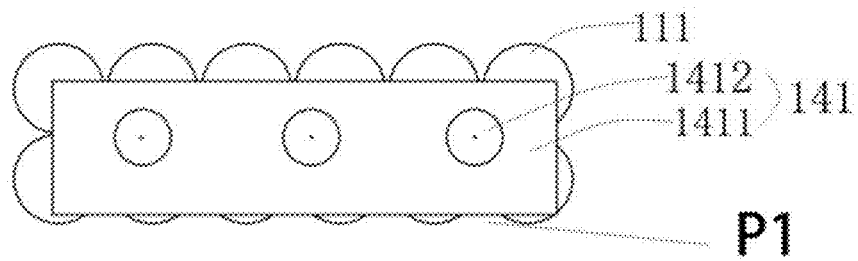
FIG. 18(a) is a schematic view of the needle piercing portion being disposed on the first end surface of the liquid guiding post according to an embodiment of the present disclosure.
Figure 18B:
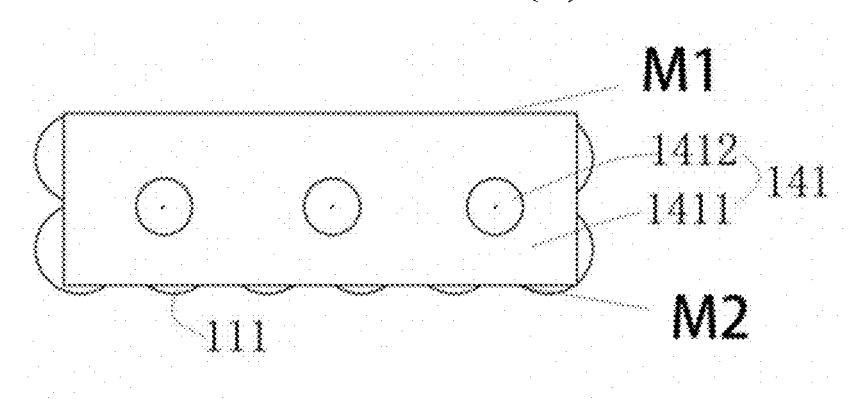
FIG. 18(b) is a schematic view of the needle piercing portion being disposed on the first end surface of the liquid guiding post according to another embodiment of the present disclosure.

The tattoo needle provided in the present disclosure, serving as a tattoo tool, may introduce the tattoo ink 300 into the superficial layer of the skin. Therefore, a liquid guiding path may be formed between the ink 300 adsorbed into the liquid guiding member 110 and the needle tooth 1412 to ensure the ink 300 in the liquid guiding member 110 to flow to the tip of the needle tooth 1412 to be further introduced into the skin. Therefore, in the tattoo needle of the present disclosure, one corner or one edge of at least one substrate 1411 of the piercing projection 141 needs to be disposed near the edge of the outer wall of the liquid guiding member 110. In this way, the needle tooth 1412 arranged on the substrate 1411 may receive the liquid flowing from the liquid guiding member 110. The above structure is necessary to effectively define the liquid guiding path to reduce the rate of empty needles. As shown in FIG. 18(a) and FIG. 18(b), the outer edge of the substrate 1411 of the piercing projection 141 has a portion that is substantially aligned with the outer edge of the liquid guiding post 111. The aligned portion ensures that the ink in the liquid guiding post 111 may flow to the tip of the needle tooth 1412.

In an embodiment, one corner or one edge of the substrate 1411 of the piercing projection 141 is substantially aligned with the edge of the outer wall of the liquid guiding member 110.

In another embodiment, the substrate 1411 of the piercing projection 141 is disposed at a middle of an end face of the liquid guiding member 110, and the corner or the edge of the substrate 1411 is no more than 0.18 mm away from the edge of the outer wall of the liquid guiding member 110.

Embodiment 9

Figure 21:
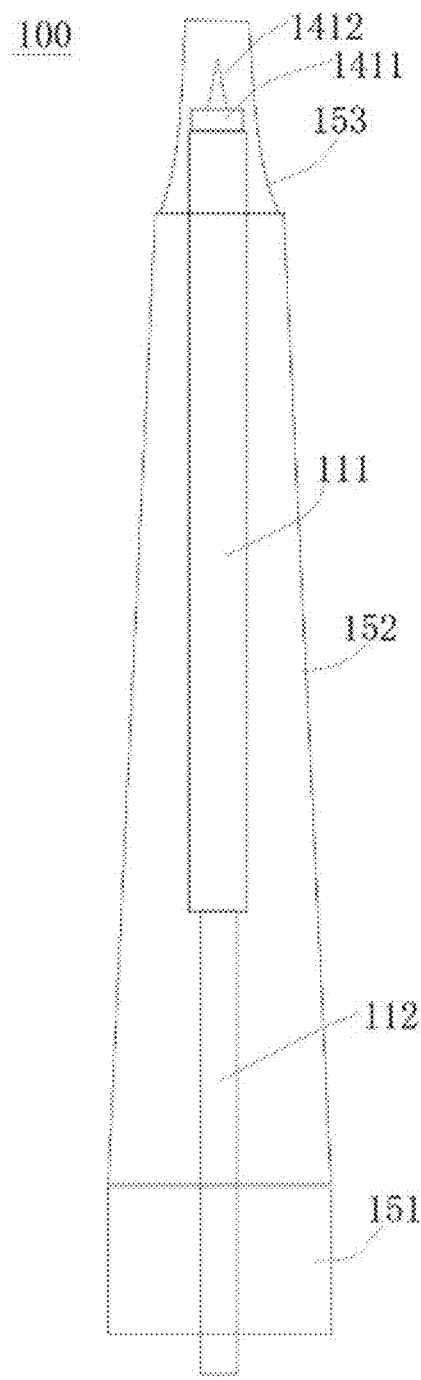
FIG. 21 is a schematic view of the tattoo needle according to an embodiment of the present disclosure, viewed from a viewing angle.
Figure 22:
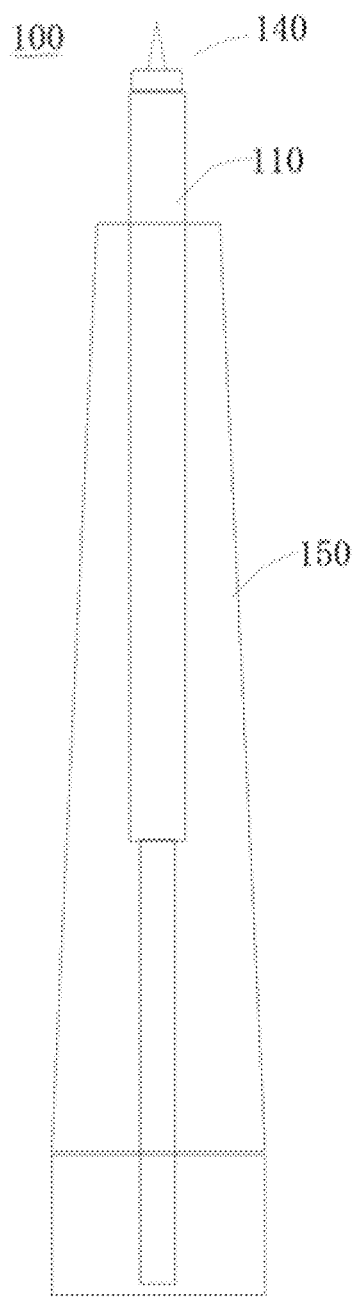
FIG. 22 is a schematic view of the structure shown in FIG. 21, omitting the needle outlet end of the case.
Figure 23:
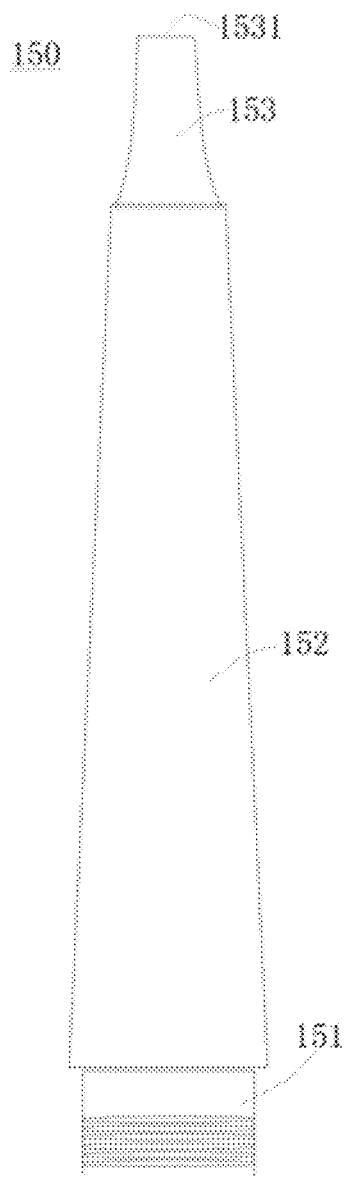
FIG. 23 is a schematic view of the case according to an embodiment of the present disclosure.

As shown in FIG. 21 to FIG. 23, the tattoo needle of the present disclosure may further be arranged with a case 150. The liquid guiding member 110 is arranged inside the case 150. The liquid guiding member 110 may move reciprocately inside the case 150 to achieve the piercing operations.

In an embodiment, the case 150 of the present disclosure may be a tubular cylinder. As shown in FIG. 10, the case 150 may have a fastening end 151, an intermediate connecting tube 152, and a needle outlet end 153. The fastening end 151, the intermediate connecting tube 152, and the needle outlet end 153 are connected to each other sequentially to define a channel for the liquid guiding member 110 to move reciprocately. Each of a central axis of the fastening end 151 and a central axis of the intermediate connecting tube 152 coincides with a central axis of the case 150.

In an embodiment, the fastening end 151 of the present disclosure is detachably connectable to an external drive member (such that the tattoo needle may be replaced easily). The needle outlet end 153 defines a needle outlet port 1531.

The needle tooth 1412 moves reciprocately at a location near the needle outlet port 1531. The liquid guiding member 110 and the needle piercing portion 140 disposed at an end of the liquid guiding member 110 are mounted, along the central axis of the case 150, in the intermediate connecting tube 152 of the case 150. The liquid guiding member 110 is disposed near the fastening end 151. The needle piercing portion 140 is disposed near the needle outlet end 153. The liquid guiding member 110 moves reciprocately in the intermediate connecting tube 152. Further, the liquid guiding member 110 drives the needle tooth 1412 of the needle piercing portion 140 to move out of the needle outlet port 1531 or to move to be retracted into needle outlet port 1531.

In an embodiment, the needle outlet end 153 of the case 150 of the present disclosure may be tubular.

The needle outlet port 1531 may have a flat port or a sloped port.

In the case that the needle outlet port 1531 is the flat port, when the liquid guiding member 110 moves freely and reciprocately at the needle outlet port 1531 of the needle outlet end 153 of the case 150, a gap between the outer wall of the liquid guiding member 110 and an inner wall of the needle outlet end 153 serves as a combined capillary space. Liquid may be temporarily stored in the combined capillary space when the needle is intaking the liquid. The liquid temporarily stored in the combined capillary may be guided by the gravitational force to flow to the needle piercing portion 140 and may be introduced into the surface layer 200 of the skin while the needle tooth 1412 of the needle piercing portion 140 is piercing into the skin.

In the case that the needle outlet port 1531 is the sloped port, when the liquid guiding member 110 is moving freely and reciprocately at the needle outlet port 1531 at the needle outlet end 153 of the case 150, a gap between the outer wall of the liquid guiding member 110 and an inner wall of the sloped port serves as a combined capillary space. Liquid is temporarily stored in the combined capillary space when the needle is intaking the liquid. The liquid temporarily stored in the combined capillary space is guided to flow to the needle piercing portion 140 and is introduced into the surface layer of the skin while the needle tooth 1412 of the needle piercing portion 140 is piercing the skin. The outer wall of the liquid guiding member 110 may abut against the inner wall of the sloped port. In this case, the sloped port serves as a limiting plate for the liquid guiding post, allowing the liquid guiding post to be vertically piercing into the skin surface layer. In an embodiment, an angle may be formed between the central axis of the case and a plane in which the plate of the sloped port is located. When the liquid guiding member is moving, the sloped port may provide abutting for the liquid guiding member.

Embodiment 10

While performing tattoo in practice, the tattoo needle is operating at a relatively high frequency. Therefore, while the needle is piercing the skin, the needle may be deviated and skewed, resulting in needle slippage. Therefore, the present disclosure provides a tattoo needle to limit the liquid guiding member 110, assisting the liquid guiding member 110 to pierce into and leave out of the skin in a straight direction, and the piercing may be accurately performed.

As shown in FIG. 24(*a*) to FIG. 24(*e*), a limiting structure 160 is arranged inside the case 150 of the introduction needle in the present embodiment. The limiting structure 160 is disposed inside the intermediate connecting tube 152 of the case 150 and/or on the fastening end 151 of the case 150 and/or on the needle outlet end 153 of the case 150. When the liquid guiding member 110 is moving reciprocately along the central axis of the case 150, the liquid guiding member 110 may abut against the limiting structure 160. The limiting structure 160 limits the liquid guiding member 110 from swinging in a direction along a cross section of the case 150. In this way, the liquid guiding member 110 drives the needle tooth 1412 of the needle piercing portion 140 to vertically move out of the case 150 to pierce into the skin surface 200. Further, the liquid guiding member 110 drives the needle tooth 1412 of the needle piercing portion 140 to vertically move from the outside of the needle outlet port 1531 to the inside of the case 150.

In an embodiment, the limiting structure 160 of the present disclosure may be a limiting hole 161. The limiting hole 161 may be a through hole. A central axis of the through hole may or may not coincide with the central axis of the liquid guiding member 110. Preferably, the central axis of the through hole does not coincide with the central axis of the liquid guiding member 110. An inner diameter of the through hole may be adapted to an outer diameter of the liquid guiding member 110. For example, a shape and a size of the central through hole may be adapted to a shape and a size of the largest cross section of the liquid guiding member 110. The adaptation in this case may not refer to the shape and the size of the through hole being identical to the shape and the size of the largest cross section of the liquid guiding member, but allows the liquid guiding member to pass through the through hole. In an embodiment, a cylindrical liquid guiding member may be adapted with a square through hole. In this case, a gap between the cylindrical liquid guiding member and the square through hole may provide the capillary effect to store the liquid, ensuring the liquid guiding member 110 to move straight in the central through hole (the limiting structure provides abutting to the liquid guiding member to limit the liquid guiding member from swinging in a lateral direction and to ensure the liquid guiding member to move straight in central through hole). In this way, the central through hole limits a position of the liquid guiding member 110. The central through hole may be circular or irregularly shaped. As shown in FIG. 11(*a*), when the through hole is irregularly shaped, the through hole may be suitable for various shapes of liquid guiding members.

In an embodiment, the limiting structure 160 of the present disclosure may be a limiting tube 162. The limiting tube 162 has a channel. A central axis of the channel may or may not coincide with the central axis of the liquid guiding member 110. An inner diameter of the channel is adapted to the outer diameter of the liquid guiding member 110. A shape and a size of the channel are adapted to the shape and the size of the largest cross section of the liquid guiding member 110. The adaptation in this case may not refer to the shape and the size of the channel being identical to the shape and the size of the largest cross section of the liquid guiding member, but allows the liquid guiding member to pass through the channel. In an embodiment, the cylindrical liquid guiding member may be adapted with a square channel. In this case, a gap between the cylindrical liquid guiding member and the square channel may provide the capillary effect to store the liquid, ensuring the liquid guiding member 110 to move straight in the central channel. The central channel limits the position of the liquid guiding member 110.

In an embodiment, as shown in FIG. 24(*e*), the limiting structure 160 of the present disclosure may be a limiting plate 164. The limiting plate 164 has a limiting surface. An angle is generated between a plane in which the limiting surface is located and the central axis of the liquid guiding member 110. In one case, the plane in which the limiting surface is located may be parallel to the central axis of the liquid guiding member 110. When the liquid guiding member 110 is moving reciprocately along the central axis of the case 150, the liquid guiding member 110 abuts against the limiting surface. The limiting surface limits the liquid guiding member 110 from swinging in the direction of the cross section of the case 150. The limiting plate 164 of the present disclosure may be disposed at the needle outlet port 1531 of the needle outlet end 153 of the case 150. One or more limiting structures 164 may be arranged. When more than one limiting structures 164 are arranged, the more than one limiting structures 164 may be evenly distributed at the needle outlet port 1531 to define a channel, and the needle piercing portion 140 may move straight in and out of the channel.

Figure 24A:
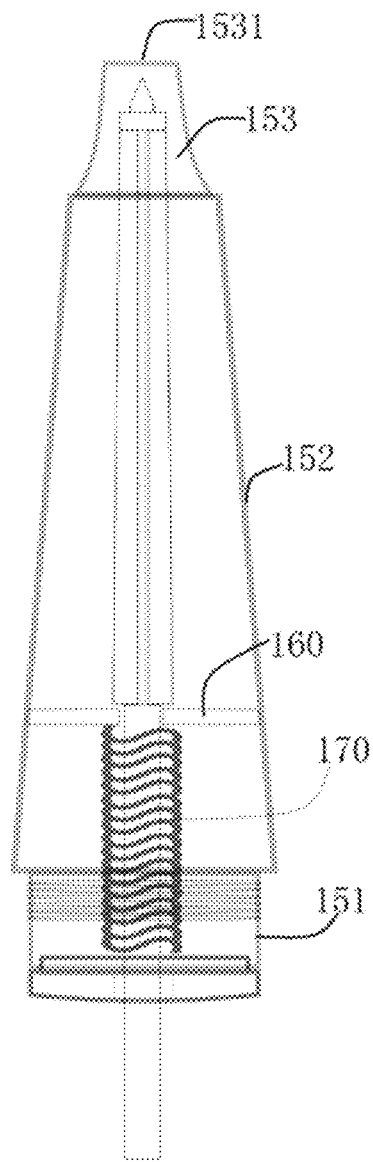
FIG. 24(a) is a schematic view of the tattoo needle according to an embodiment of the present disclosure.
Figure 24B:
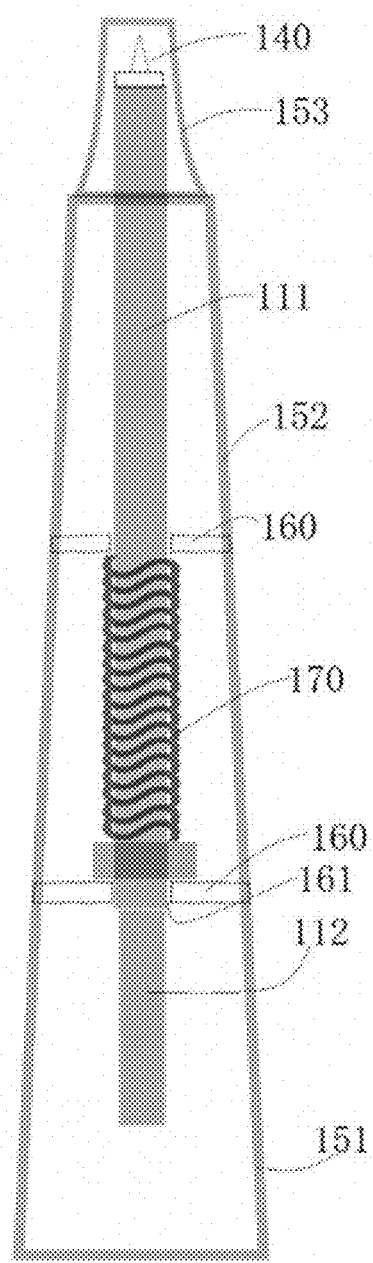
FIG. 24(b) is another schematic view of the tattoo needle according to an embodiment of the present disclosure.
Figure 24C:
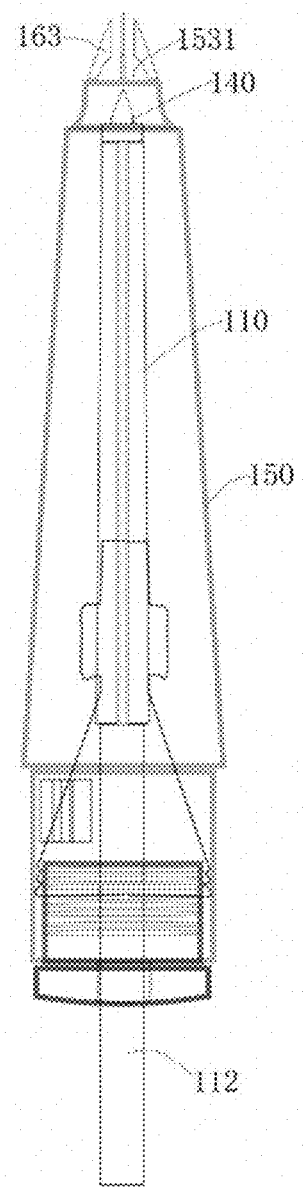
FIG. 24(c) is another schematic view of the tattoo needle according to an embodiment of the present disclosure.
Figure 24D:
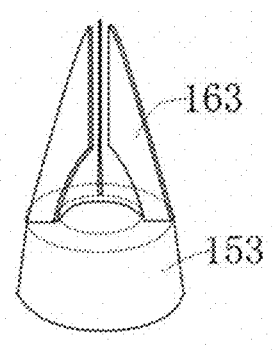
FIG. 24(d) is a perspective view of the needle outlet end of the introduction needle shown in FIG. 24(c).
Figure 24E:
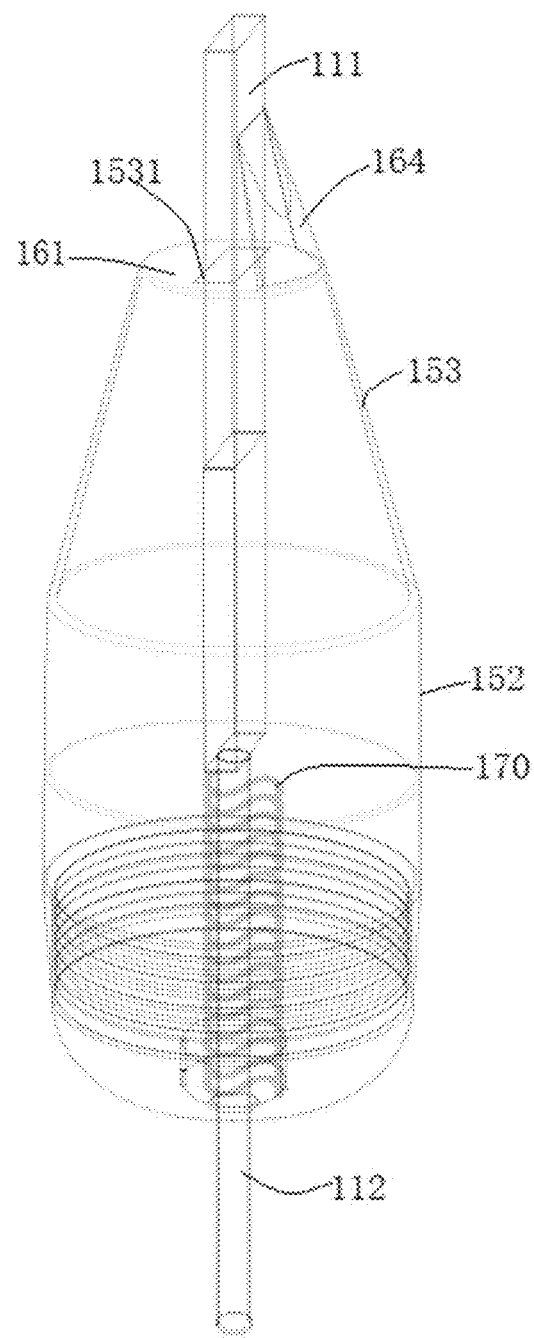
FIG. 24(e) is a schematic view of the tattoo needle according to an embodiment of the present disclosure.

As shown in FIG. 24(c) and FIG. 24(d), in an embodiment, the limiting structure 160 of the present disclosure may be a limiting bracket 163. The limiting bracket 163 is disposed at an end of the case 150 (or disposed inside the case). The limiting bracket 163 includes one or more sub-brackets. For each of the one or more sub-brackets, a side of the sub-bracket abuts against the liquid guiding member 110. The sub-brackets limit the liquid guiding member 110 from swinging in the direction of the cross section of the case 150. When the liquid guiding member 110 moves reciprocately along the central axis of the case 150, the liquid guiding member 110 abuts against a side of the sub-bracket. Further, due to abutting against the side of the sub-bracket, the liquid guiding member 110 is guided to move to the needle outlet port 1531 of the case 150.

The limiting structure 160 in the present embodiment may effectively limit and guide the liquid guiding member 110, ensuring the needle to pierce the skin at desired position accurately and preventing the needle from being skewed or from slipping.

Embodiment 11

As shown in FIG. 24(a) to FIG. 24(c), the introduction needle 100 in the present embodiment may further include an elastic member 170, such as a spring, a silicone member, or a rubber band. An end of the elastic member 170 is connected to the case 150, and the other end of the elastic member 170 is connected to the connecting rod of the liquid guiding member 110. The elastic member may be connected to the case or the liquid guiding member in various ways, such as connection by abutting, encased connection, or connection by hooks, and so on. The case 150 is connected to the motorized rod. When the liquid guiding member 110 is driven by an external force (a motor of the motorized rod is activated to apply a driving force to the liquid guiding member 110) to move along the central axis of the case 150 towards the needle outlet port 1531 of the case 150, the elastic member 170 is elastically deformed to drive the liquid guiding member 110 to move back to its initial position.

Embodiment 12

Different tattoo patterns and tattoo locations may require different tattoo needles to be used. The present disclosure further provides a tattoo needle 100, and the piercing projection 141 of the tattoo needle includes one substrate 1411 and one needle tooth 1412 arranged on the substrate 1411. The tattoo needle having one needle tooth 1412 is more suitable to pierce the skin at a sing dot to form a tattoo pattern.

The plurality of needles arranged in a row as described in the present disclosure may be used to tattoo a relatively long linear pattern having a small transition arc. Compared to the needle having a single needle tooth, the needle having a plurality of needles arranged in a row may produce the tattoo having this specific pattern more efficiently. Of course, for dots or patterns having large transition arcs between lines, the needle having a single needle tooth needle is more advantageous.

Embodiment 13

Figure 25:
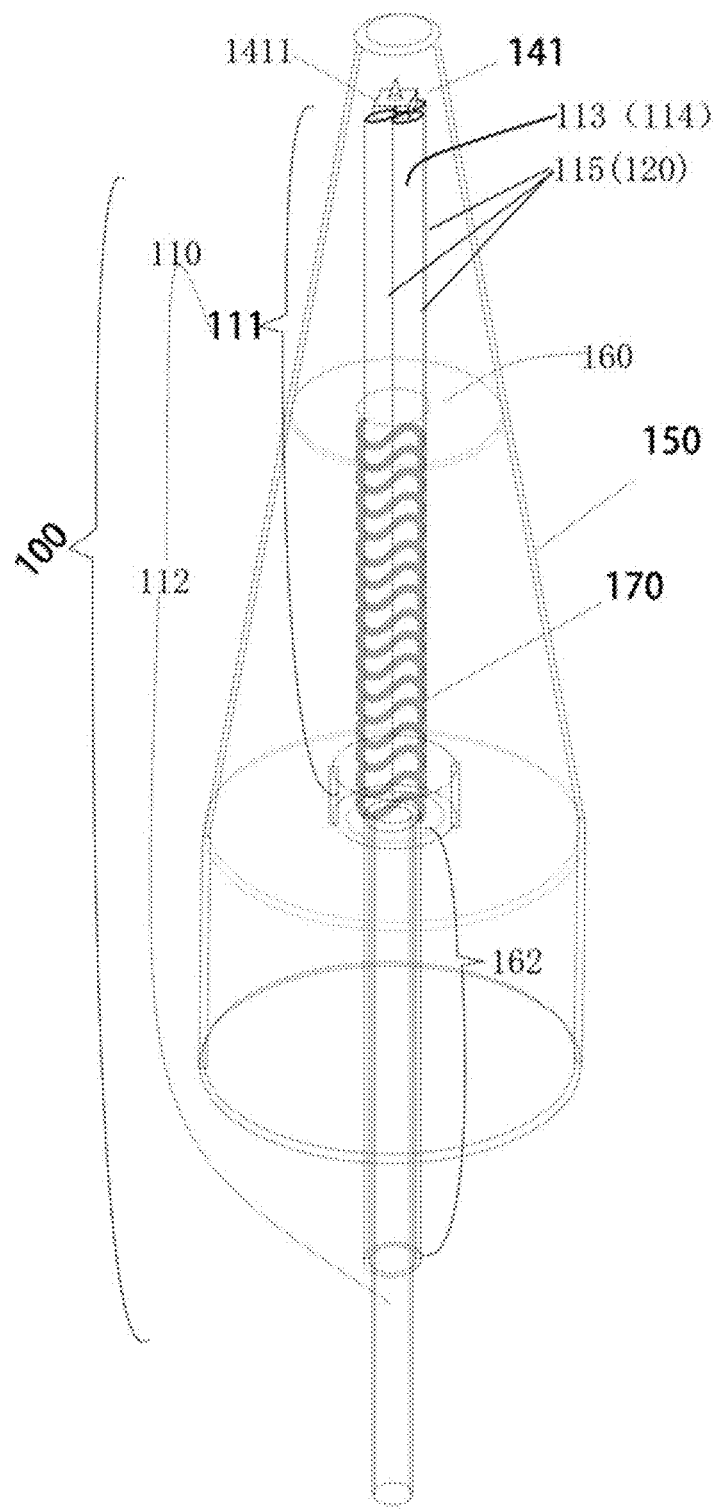
FIG. 25 is a schematic view of the tattoo needle according to an embodiment of the present disclosure.

Based on the tattoo needle of the present embodiment, the present disclosure further provides a tattoo device. As shown in FIG. 25, the tattoo device includes any one of the above-mentioned tattoo needles 100 and an external drive member that drives the liquid guiding member 110 of the introduction needle 100 to move.

In an embodiment, the external drive member includes a manual rod, a motorized rod, and an intelligent arm.

After producing the tattoo by applying the tattoo needle in the present disclosure, the essential components for breaking the skin may be functionally destroyed, reducing accidental injuries and eliminating reusage, improving safety of the tattoo tool and environmental protection.

In the description of the present disclosure, the terms "an embodiment", "some embodiments", "examples", "specific examples", or "some examples" mean that specific features, structures, materials or characteristics described in one embodiment or one example are included in at least one embodiments or examples of the present disclosure. In the present specification, exemplary expressions of the above terms may not be directed to the same embodiment or the same example. Moreover, the specific features, structures, materials, or characteristics described may be combined in any one or more embodiments or examples in a suitable manner. In addition, any ordinary skilled person in the art may join and combine different embodiments or examples described in the present specification.

Although embodiments of the present disclosure have been shown and described above, it is to be understood that the above embodiments are exemplary and are not to be interpreted as a limitation of the present disclosure. Any ordinary skilled person in the art may perform changes, modifications and variations on the above embodiments within the scope of the present disclosure.

What is claimed is:

1. A tattoo needle, comprising: a needle piercing portion and a liquid guiding member,
    wherein the needle piercing portion comprises at least one piercing projection, wherein each of the at least one piercing projection comprises at least one substrate and a plurality of needle teeth;
    the plurality of needle teeth is arranged on a side surface of one substrate, the plurality of needle teeth is arranged in a row on the substrate, a central axis of each of the plurality of needle teeth is perpendicular to the side surface of the one substrate; and the one substrate is configured to limit a piercing depth when the plurality of needle teeth pierces into a skin;
    wherein the liquid guiding member is columnar, the other side surface of the other side of the substrate is fixed to an end of the columnar liquid guiding member, a central axis of the columnar liquid guiding member is parallel to the central axis of each of the plurality of needle teeth.

2. The tattoo needle according to claim 1, wherein the liquid guiding member is arranged with a capillary liquid storage unit configured to store liquid, the liquid guiding member is configured to guide the liquid flow to the needle piercing portion; and when the plurality of needle teeth pierces into a surface of the skin, the liquid is capable of being introduced into the surface of the skin along the plurality of needle teeth.

3. The tattoo needle according to claim 1, wherein when the number of the at least one substrate is more than one, and the plurality of needle teeth are arranged on each of the more than one substrates; and, on each of the more than one substrates, the plurality of needle teeth are spaced apart from each other.

4. The tattoo needle according to claim 3, wherein, for each of the more than one substrates, a center spacing between two adjacent needle teeth of the plurality of needle teeth is in a range from 0-1500 μm; and the more than one substrates and the plurality of needle teeth are configured as a one-piece and integral structure.

5. The tattoo needle according to claim 3, wherein each of the plurality of needle teeth is a protrusion protruding from the substrate, and a size of a cross sectional area of the protrusion decreases in a direction from the substrate towards a free end of the protrusion away from the substrate;

for each of the plurality of needle teeth, a bottom face of the needle tooth is connected to a corresponding one of the more than one substrates, the free end of the needle tooth is a top end, a height of the needle tooth is in a range from 50 μm to 1,500 μm, and a diameter of the bottom face of the needle tooth is in a range from 50 μm to twice the height of the needle tooth.

6. The tattoo needle according to claim 5, wherein each of the plurality of needle teeth comprises a tail pin and a top pin integrally formed with an end of the tail pin, the tail pin is columnar, the top pin is protruding from the tail pin, a size of a cross sectional area of the top pin decreases in a direction extending from the tail pin to a free end of the top pin away from the tail pin, and the other end of the columnar tail pin is fixedly connected to the corresponding one of the more than one substrates.

7. The tattoo needle according to claim 2, wherein one corner or one edge of the one substrate of the at least one piercing projection is disposed near an edge of an outer wall of the liquid guiding member, and the plurality of needle teeth arranged on the one substrate is configured to receive liquid flowing from the liquid guiding member.

8. The tattoo needle according to claim 3, wherein the one corner or the one edge of the substrate of the at least one piercing projection is aligned with or is in no more than 0.18 mm away from the edge of the outer wall of the liquid guiding member.

9. A tattoo needle, comprising a liquid guiding member and a needle piercing portion arranged at an end of the liquid guiding member, wherein the liquid guiding member comprises a liquid guiding post, the liquid guiding post comprises a capillary liquid storage unit to store liquid, the liquid guiding post is configured to guide liquid flow to the needle piercing portion; and when the needle piercing portion pierces into a surface of a skin, the liquid is being capable of being introduced into the surface of the skin;

wherein the needle piercing portion comprises at least one piercing projection, the piercing projection comprises a substrate and a needling tooth arranged on a side surface of the substrate, the liquid guiding member is columnar, the other side surface of the other side of the substrate is fixed to an end of the columnar liquid guiding member, a central axis of the columnar liquid guiding member is parallel to a central axis of the needling tooth.

10. The tattoo needle according to claim 9, wherein the liquid guiding member comprises the liquid guiding post and a connecting rod connected to the liquid guiding post, the connecting rod is connected to a drive portion, the liquid guiding member is configured to be driven by the drive portion to move reciprocately along the central axis of the liquid guiding member.

11. The tattoo needle according to claim 9, wherein the liquid guiding post defines a plurality of channels, the plurality of channels are defined in an outer wall of the liquid guiding post and/or in an interior of the liquid guiding post, the plurality of channels cooperatively serves as the capillary liquid storage unit; and at least one of the plurality of channels is configured to store liquid, and the liquid in the at least one of the plurality of channels is capable of being guided to flow to the needle tooth.

12. The tattoo needle according to claim 11, wherein each of the plurality of channels extends from a first end face towards a second end face.

13. The tattoo needle according to claim 11, wherein the liquid guiding post comprises a plurality of small sub-posts arranged adjacent to each other, a gap defined between adjacent two of the plurality of small sub-posts serves as any of the plurality of channels, serving as the capillary liquid storage unit.

14. The tattoo needle according to claim 9, wherein the liquid guiding post is arranged with a liquid storage structure on an outer wall of the liquid guiding post, the liquid storage structure comprises one or more sheets, the one or more sheets are attached to the outer wall of the liquid guiding post, a gap is defined between the one or more sheets and the outer wall of the liquid guiding post and serves as the capillary storage unit; and when liquid is stored in the capillary storage unit, the liquid is capable of being guided to flow to the needle piercing portion.

15. The tattoo needle according to claim 9, wherein one corner or one edge of the substrate of the at least one piercing projection is disposed near the edge of the outer wall of the liquid guiding member, and the needle tooth arranged on the substrate is configured to receive liquid flowing from the liquid guiding member.

16. The tattoo needle according to claim 9, further comprising a case, wherein the case is a tubular cylinder, the case has a fastening end, an intermediate connecting tube, and a needle outlet end; the fastening end, the intermediate connecting tube and the needle outlet end are connected with each other in sequence to form a channel in which the liquid guiding member is configured to move reciprocately; each of a central axis of the fastening end and a central axis of the intermediate connecting tube coincides with a central axis of the case;

the fastening end is detachably connected to an external drive member, the needle outlet end defines a needle outlet port; and the liquid guiding member and the piercing projection are mounted in the intermediate connecting tube of the case along the central axis of the case, the piercing projection is disposed near the needle outlet end, the liquid guiding member is configured to move reciprocately in the intermediate connecting tube and is configured to drive the piercing projection to move to an outside or to retract the piercing projection to an inside of the needle outlet port.

17. The tattoo needle according to claim 16, wherein the case is arranged with a limiting structure, the limiting structure is disposed inside the intermediate connecting tube of the case and/or on the fastening end of the case and/or at the needle outlet end of the case;

when the liquid guiding member moves reciprocately along the central axis of the case, the liquid guiding member abuts against the limiting structure, and the limiting structure is configured to limit the liquid guiding member from swinging in a direction of a cross section of the case, and the liquid guiding member is configured to drive the piercing projection to move vertically out of the case to pierce into the surface of the skin and configured to retract the piercing projection vertically to the inside of the needle outlet port.

18. The tattoo needle according to claim 16, further comprising an elastic member, wherein an end of the elastic member is connected to the case, and the other end of the elastic member is connected to the liquid guiding member; when the liquid guiding member is driven by an external force to move along the central axis of the case towards the needle outlet port, the elastic member is elastically deformed to drive the liquid guiding member to move back to an initial position of the liquid guiding member.

19. A tattoo device, comprising a tattoo needle and an external drive member, wherein, wherein the tattoo needle comprises a liquid guiding member and a needle piercing portion arranged at an end of the liquid guiding member, wherein the liquid guiding member comprises a liquid guiding post, the liquid guiding post comprises a capillary liquid storage unit to store liquid, the liquid guiding post is configured to guide liquid flow to the needle piercing portion; and when the needle piercing portion pierces into a surface of a skin, the liquid is being capable of being introduced into the surface of the skin; and the external drive member is configured to drive the liquid guiding member of the tattoo needle to move;

wherein the needle piercing portion comprises at least one piercing projection, the piercing projection comprises a substrate and a needling tooth arranged on a side surface of the substrate, the liquid guiding member is columnar, the other side surface of the other side of the substrate is fixed to an end of the columnar liquid guiding member, a central axis of the columnar liquid guiding member is parallel to a central axis of the needling tooth.

* * * * *